(12) United States Patent
Agoston et al.

(10) Patent No.: US 7,087,592 B1
(45) Date of Patent: Aug. 8, 2006

(54) COMPOSITIONS COMPRISING PURIFIED 2-METHOXYESTRADIOL AND METHODS OF PRODUCING SAME

(75) Inventors: Gregory E. Agoston, Germantown, MD (US); Jamshed H. Shah, Brookeville, MD (US); Anthony M. Treston, Rockville, MD (US)

(73) Assignee: Entre Med, Inc., Rockville, MD (US)

( * ) Notice: Subject to any disclaimer, the term of this patent is extended or adjusted under 35 U.S.C. 154(b) by 566 days.

(21) Appl. No.: 09/644,387

(22) Filed: Aug. 23, 2000

Related U.S. Application Data

(60) Provisional application No. 60/150,293, filed on Aug. 23, 1999.

(51) Int. Cl.
*A61K 31/56* (2006.01)
(52) U.S. Cl. ..................................................... 514/182
(58) Field of Classification Search ................. 514/182
See application file for complete search history.

(56) References Cited

U.S. PATENT DOCUMENTS

| | | | |
|---|---|---|---|
| 2,584,271 A | 2/1952 | Huffman | |
| 2,846,453 A | 8/1958 | Hoehn | |
| 3,166,577 A | 1/1965 | Ringold et al. | |
| 3,410,879 A | 11/1968 | Smith et al. | |
| 3,470,218 A | 9/1969 | Farah | |
| 3,492,321 A | 1/1970 | Crabbe | |
| 3,496,272 A | 2/1970 | Kruger | |
| 3,562,260 A | 2/1971 | De Ruggieri et al. | |
| 3,956,348 A | 5/1976 | Hilscher | |
| 4,172,132 A | 10/1979 | Draper et al. | |
| 4,212,864 A | 7/1980 | Tax | |
| 4,307,086 A | 12/1981 | Tax | |
| 4,444,767 A | 4/1984 | Torelli et al. | |
| 4,522,758 A | 6/1985 | Ward et al. | |
| 4,552,758 A | 11/1985 | Murphy et al. | |
| 4,634,705 A | 1/1987 | DeBernardis et al. | |
| 4,743,597 A | 5/1988 | Javitt et al. | |
| 4,808,402 A | 2/1989 | Leibovich et al. | |
| 4,994,443 A | 2/1991 | Folkman et al. | |
| 5,001,116 A | 3/1991 | Folkman et al. | |
| 5,135,919 A | 8/1992 | Folkman et al. | |
| 5,504,074 A * | 4/1996 | D'Amato et al. ............ 514/182 |
| 5,521,168 A * | 5/1996 | Clark ......................... 514/178 |
| 5,621,124 A | 4/1997 | Seilz et al. | |
| 5,629,327 A | 5/1997 | D'Amato | |
| 5,629,340 A | 5/1997 | Kuwano et al. | |
| 5,639,725 A | 6/1997 | O'Reilly et al. | |
| 5,643,900 A * | 7/1997 | Fotsis et al. ................ 514/182 |
| 5,646,136 A | 7/1997 | Petrow | |
| 5,661,143 A | 8/1997 | D'Amato et al. | |
| 5,716,981 A | 2/1998 | Hunter et al. | |
| 5,733,876 A | 3/1998 | O'Reilly et al. | |
| 5,763,432 A | 6/1998 | Tanabe et al. | |
| 5,776,704 A | 7/1998 | O'Reilly et al. | |
| 5,792,845 A | 8/1998 | O'Reilly et al. | |
| 5,837,682 A | 11/1998 | O'Reilly | |
| 5,854,205 A | 12/1998 | O'Reilly et al. | |
| 5,854,221 A | 12/1998 | Cao et al. | |
| 5,861,372 A | 1/1999 | Folkman et al. | |
| 5,885,795 A | 3/1999 | O'Reilly et al. | |
| 5,892,069 A | 4/1999 | D'Amato et al. | |
| 5,919,459 A | 7/1999 | Nacy et al. | |
| 5,958,892 A | 9/1999 | Mukhopadhyay et al. | |
| 6,011,023 A | 1/2000 | Clark et al. | |
| 6,046,186 A | 4/2000 | Tanabe et al. | |
| 6,051,726 A | 4/2000 | Sachdeva et al. | |
| 6,054,598 A | 4/2000 | Sachdeva et al. | |
| 6,136,992 A | 10/2000 | Ram et al. | |
| 6,200,966 B1 * | 3/2001 | Stewart ....................... 514/178 |
| 6,239,123 B1 | 5/2001 | Green et al. | |
| 6,284,789 B1 | 9/2001 | LaLonde et al. | |
| 6,346,510 B1 | 2/2002 | O'Reilly et al. | |
| 6,399,773 B1 | 6/2002 | Liu et al. | |
| 6,410,029 B1 | 6/2002 | Mukhopadhyay et al. | |
| 6,413,513 B1 | 7/2002 | Holaday | |
| 6,514,971 B1 | 2/2003 | Thomas et al. | |
| 6,528,676 B1 | 3/2003 | D'Amato et al. | |
| 6,605,622 B1 | 8/2003 | Green et al. | |
| 6,723,858 B1 | 4/2004 | D'Amato et al. | |
| 6,730,665 B1 | 5/2004 | Maran et al. | |
| 6,908,910 B1 | 6/2005 | D'Amato et al. | |

(Continued)

FOREIGN PATENT DOCUMENTS

EP  0166937 A2  8/1986

(Continued)

OTHER PUBLICATIONS

Nambara, T., et al., "Studies on Steroid Conjugates. III. New Syntheses of 2-Methoxyestrogens" *Chem. Pharm. Bull.*, vol. 18, No. 3, pp. 474-480 (1970).

(Continued)

*Primary Examiner*—Barbara P. Badio
(74) *Attorney, Agent, or Firm*—Kilpatrick Stockton LLP

(57) ABSTRACT

2-methoxyestradiol having greater than 98% purity is obtained by synthetic or purification methods. This highly pure 2-methoxy estradiol, lacking estrogenic components, is particularly suitable for clinical use in humans. The purification methods of the invention involve the use of liquid-solid chromatography (LSC) to separate 2-ME2 from other compounds. The chromatographic media is preferably silica. The solvent system comprises a non-polar solvent, such as chloroform, and a polar solvent, such as methanol.

25 Claims, 16 Drawing Sheets

U.S. PATENT DOCUMENTS

| | | |
|---|---|---|
| 2002/0002294 A1 | 1/2002 | D'Amato et al. |
| 2002/0165212 A1 | 11/2002 | D'Amato et al. |
| 2003/0027803 A1 | 2/2003 | Slaga et al. |
| 2003/0096800 A1 | 5/2003 | D'Amato et al. |
| 2003/0236408 A1 | 12/2003 | D'Amato et al. |
| 2004/0072813 A1 | 4/2004 | D'Amato et al. |
| 2004/0214807 A1 | 10/2004 | D'Amato et al. |
| 2005/0020555 A1 | 1/2005 | D'Amato et al. |

FOREIGN PATENT DOCUMENTS

| | | |
|---|---|---|
| EP | 0657175 A2 | 6/1995 |
| GB | 857080 | 12/1960 |
| GB | 857081 | 12/1960 |
| GB | 1570597 | 7/1980 |
| JP | 39-5480 B | 4/1939 |
| JP | 41 000100 A | 1/1966 |
| JP | 42-928 B | 1/1967 |
| JP | 58-131978 | 8/1983 |
| JP | 63090763 A | 4/1988 |
| JP | 63-119500 | 5/1988 |
| JP | 09316000 A | 9/1997 |
| JP | 11-209322 | 8/1999 |
| SU | 1240038 A1 | 10/1996 |
| WO | WO 87/02367 A3 | 4/1987 |
| WO | WO 88/08002 A1 | 10/1988 |
| WO | WO 90/15816 | 12/1990 |
| WO | WO 93/03729 | 3/1993 |
| WO | WO 93/19746 A1 | 10/1993 |
| WO | WO 95/04535 | 2/1995 |
| WO | WO 98/32763 A1 | 7/1998 |
| WO | WO 98/40398 | 9/1998 |
| WO | WO 99/01142 A1 | 1/1999 |
| WO | WO 99/22728 A1 | 5/1999 |
| WO | WO 99/33858 A3 | 7/1999 |
| WO | WO 99/33859 A2 | 7/1999 |
| WO | WO 99/35150 A3 | 7/1999 |
| WO | WO 99/45018 A1 | 9/1999 |
| WO | WO 00/07576 A2 | 2/2000 |
| WO | WO 00/10552 A2 | 3/2000 |
| WO | WO 00/66095 A2 | 11/2000 |
| WO | WO 00/68246 A1 | 11/2000 |

OTHER PUBLICATIONS

Napolitano, et al., "11 Beta-Substituted Estradiol Derivatives. 2. Potential Carbon-11-and Inodine-Labeled Probes for the Estrogen Receptor", *J. Med. Chem.*, vol. 38, No. 14, pp. 2774-2779 (Jul. 7, 1995) (Abstract Only).

Nishigaki, et al., "Anti-Proliferative Effect of 2-Methoxyestradiol on Cultured Smooth Muscle Cells from Rabbit Aorta", *Atherosclerosis*, vol. 113, pp. 167-170 (1995).

Numazawa M. et al., "Efficient Synthesis of 2-Methoxy- and 4-Methoxy-Estrogens" *J. Chem. Soc.*, pp. 533-534 (1983).

Oppolzer, et al., "177.The Enantioslective Synthesis of (+)-Estradiol from 1,3-Dihydrobenzo[c]thiophene-2,2-dioxide by Successive Thermal $SO_2$-Extrusion and Cycloaddition Reactions", *Helvetica Chimica Acta*, vol. 63, pp. 1703-1707 (1980).

Parthasarathy, et al., "Antioxidant: A New Role for RU-486 and Related Compounds", *J. Clin. Invest.*, vol. 94, No. 5, pp. 1990-1995 (1994) (Abstract Only).

Paull, et al., "Identification of Novel Antimitotic Agents Acting at the Tubulin Level by Computer-assisted Evaluation of Differential Cytotoxicity Data", *Cancer Research*, vol. 52, pp. 3892-3900 (Jul. 15, 1992).

Poli et al., "Tumor Necrosis Factor α Functions in an Autocrine Manner in the Induction of Human Immunodeficiency Virus Expression", *Proc. Natl. Acad. Sci. USA*, vol. 87, pp. 782-785 (Jan. 1990).

Rao, et al., "Structural Specificity of Estrogens in the Induction of Mitotic Chromatid Non-Disjunction in Hela Cells", *Experimental Cell Research*, vol. 48, pp. 71-81 (1967).

Rao, et al., "A Novel, Two-Step Synthesis of 2-Methoxyestadiol" *Synthesis*, pp. 168-169 (Mar. 1977).

Ravindra, R., "Effect of Estradiol on the *in vitro* Assembly of Rat Brain Tubulin", *J. Indian Inst. Sci.*, vol. 64, No. 3, pp. 27-35 (1983).

Sakakibara et al., "Effects of Diethylstilbestrol and its Methyl Ethers on Aneuploidy Induction and Microtubule Distribution in Chinese Hamster V79 cells", *Mutation Research*, vol. 263, pp. 269-276 (1991).

Sato et al., "Effect of Estradiol and Ethynylestradiol on Microtubule Distribution in Chinese Hamster V79 Cells", *Chem. Pharm. Bull.*, vol. 40, No. 1, pp. 182-184 (1992).

Sato et al., "Disruptive Effect of Diethylstillbestrol on Microtubules", *Gann*, vol. 75, pp. 1046-1048 (1984).

Adams, E.F. et al., "Steroidal regulation of oestradiol-17B dehydrogenase activity of the human breast cancer cell line MCF-7", *Journal of Endocrinology*, vol. 188, pp. 149-154 (Jul. 1988).

Aizu-Yokota, et al., "Natural Estrogens Induce Modulation of Microtubules in Chinese Hamster V79 Cells in Culture", *Cancer Research*, vol. 55, pp. 1863-1868 (May 1, 1995).

Attalla, et al., "2-Methoxyestradiol Arrests Cells in Mitosis without Depolymerizing Tubulin", *Biochem. and Biophys. Resch. Comm.*, vol. 228, pp. 467-473 (1996).

Ayala, et al. "The Induction of Accelerated Thymic Programmed Cell Death During Polymicrobial Sepsis: Control by Corticosteroids but not Tumor Necrosis Factor", *Shock*, vol. 3, No. 4, pp. 259-267 (Apr. 1995) (Abstract Only).

Banik, et al., "Orally Active Long-Acting Estrogen (3-(2-propynloxy)-estra-1,3,5 (10)—trien—17.beta.-oltrimethylacetate)", *Steroids*, vol. 16, No. 3, pp. 289-296 (1970) (Identifier Only).

Bardon, et al., "Steroid Receptor-Mediated Cytotoxicity of an Antiestrogen and an Antiprogestin in Breast Cancer Cells", *Cancer Researcher*, vol. 47, No. 5, pp. 1441-1448 (Mar. 1, 1987) (Abstract Only).

Bhat, et al., "Estradiol-induced Mitotic Inhibition in the Bursa of Fabricius of Male Domestic Duckling", *Mikroskopie*, vol. 39, pp. 113-117 (May 1982).

Blagosklonny, et al. "Raf-1/bcl-2 Phosphorylation: A Step from Microtubule Damage to Cell Death", *Cancer Research*, vol. 57, pp. 130-135 (Jan. 1, 1997).

Blickenstaff, et al., "Estrogen-Catharanthus (Vinca) Alkaloid Conjugates", *Cytotoxic Estrogens in Hormone Receptive Tumors*, Academic Press, pp. 89-105 (1980).

Boyé et al., "185. Deaminocolchinyl Methyl Ether: Synthesis from 2,3,4,4'-Tetramethoxybiphenyl-2-carbaldehyde Comparison of Antitubulin Effects of Deaminocolchinyl Methyl Ether and Dehydro Analogs", *Helvetica Chimica Acta*, vol. 72, pp. 1690-1696 (1989).

Brodie, A.M., "Aromatase Inhibitiors in the Treatment of Breast Cancer", *J.Steroid Biochem. Mol. Biol.*, vol. 49, Nos. 4-6, pp. 281-287 (Jun. 1994) (Abstract Only).

Brosens, et al., "Comparative Study of the Estrogenic Effect of Ethinylestradiol and Mestranol on the Endometrium" Laboratory fore Gynecological Physiopathology, vol. 14, No. 6, pp. 679-685 (Dec. 1976).

Castagnetta, Luigi, et al. "Simple Approach to Measure Metabolic Pathways of Steroid in Living Cells", *J. Chromatogr.*, vol. 572, pp. 25-39 (1991).

Chasserot-Golaz, et al., "Biotransformation of 17.beta.-hydroxy-11.beta.-(4-dimethylaminophenyl) 17.alpha.1-propynyl-estra-4, 9-dien-3-one (RU486)in Rat Hepatoma Variants", *Biochem. Pharmacol.*, vol. 46, No. 11, pp. 2100-2103 (1993) (Identifier Only).

Chen, et al., "A New Synthetic Route to 2- and 4-Methoxyestradiols by Nucleophilic Substitution" *Steroids*, vol. 47, No. 1, pp. 63-66 (Jan. 1986).

Chen, et al., "Synthesis of 11.beta.-(4-dimethylaminophenyl)-17.beta.-hydroxy-17.alpha.1(1-propynl) estra-4, 9-dien-3-one (RU486)", *Nanjing Yaoxueyuan Xuebao*, vol. 17, No. 4, pp. 282-285 (1986) (Identifier Only).

Cohen et al., "Novel Total Synthesis of (+)-Estrone 3-Methyl Ether,(+)-13B-Ethyl-3-methoxygona-1,3,5(10-triene-17-one, and (+)-Equilenin 3-Methyl Ether", The Journal of Organic Chemistry, vol. 6, pp. 681-685 (Mar. 21, 1975).

Collins, et al., "The Structure and Function of Estrogens. XI* Synthesis of (=/−)-7(8-11α)-abeo-Estradiol and its 9,11-Didehydro Derivative" Aust. J. Chem., vol. 45, pp. 71-97 (1992).

Cummings, et al., "Apoptosis", *Am J. of Surgical Pathology*, vol. 21, No. 1, pp. 88-101 (1997).

Crum et al., "A New Class of Steroids Inhibits Angiogenesis in the Presence of Heparin or a Heparin Fragment", *Science*, vol. 230, pp. 1375-1378 (Dec. 20, 1985).

Cushman, et al., "Synthesis of Analogs of 2-Methoxyestradiol with Enhanced Inhibitory Effects on Tubulin Polymerization and Cancer Cell Growth", *J. Med. Chem.*, vol. 40, No, 15, pp. 2323-2334 (Jul. 1997) (Abstract Only).

Cushman, et al., "Synthesis Antitiubulin and Antimitotic Activity, and Cytotoxicity of Analogs of 2-Methoxyestradiol, an Endogenous Mammalian Metabolite of Estradiol that Inhibits Tubulin Polymerization by Binding to the Colchicine Bindng Site", *J. Med. Chem.*, vol. 38, No. 12, pp. 2041-2049 (1995).

D'Amato, et al., "2-Methoxyestradiol, an Endogenous Mammalian Metabolite, Inhibits Tubulin Polymerization by Interacting at the Colchicine Site", *Proc. Natl. Acad. Sci.*, vol. 91, pp. 3964-3968 (Apr. 1994).

Dvir, et al., "Thin-layer Chromatography of DANSYL-oestrogens", *J. Chromatog.* vol. 52, pp. 505-506 (1970).

Epe, et al., "Microtubular Proteins as Cellular Targets for Carcinogenic Estrogens and Other Carcinogens" Mechanisms of Chromosome Distribution and Aneuploidy, pp. 345-351 (1989).

Evans et al., "A Convergent Total Synthesis of (+)-Colchicine and (+)—Desacetamidoisocolchicine", *J. Am. Chem. Society*, vol. 103, pp. 5813-5821 (1981).

Fishman, Jack, "Synthesis of 2-Methoxyestrogens", J. Am. Chem. Soc., vol. 80, pp. 1213-1216 (1958).

Fitzgerald, "Molecular Features of Colchicine Associated with Antimitotic Activity and Inhibition of Tubulin Polymerization", *Biochem. Pharmacol*, vol. 25, pp. 1383-1387 (1976).

Fotsis, et al., "The Endogenous Oestrogen Metabolite 2-Methoxyoestradiol Inhibits Angiogenesis and Suppresses Tumour Growth", *Nature*, vol. 368, pp. 237-239 (Mar. 17, 1994).

Getahun et al. "Synthesis of Alkoxy-Substituted Diaryl Compounds and Correlation of Ring Separation with Inhibition of Tubulin Polymerization: Differential Enhancement of Inhibitory Effects Under Suboptimal Polymerization Reaction Conditions", *J. Med. Chem.*, vol. 35, pp. 1058-1067 (Mar. 20, 1992).

Gross, et al., "Inhibition of Tumor Growth, Vascularization, and Collagenolysis in the Rabbit Cornea by Medroxyprogesterone", *Proc. Natl. Acad. Sci. USA*, vol. 78, No. 2, pp. 1176-1180 (Feb. 1981).

Haldar, et al., "Bcl2 is the Guardian of Microtubule Integrity", *Cancer Research*, vol. 57, pp. 229-233 (Jan. 15, 1997).

Hamel, et al., "Interactions of 2-Methoxyestradiol, an Endogenous Mammalian Metabolite, with Unpolymerized Tubulin and with Tubulin Polymers", *Biochemistry*, vol. 35, No. 4, pp. 1304-1310 (1996).

Hartley-Asp et al., "Diethylstilbestrol Induces Metaphase Arrest and Inhibits Microtubule Assembly", *Mutation Research*, vol. 143, pp. 231-235 (1985).

He, Hu-Ming et al., "A Versatile Synthesis of 2-Methoxyestradiol, an Endogenous Metabolite of Estradiol Which Inhibits Tubulin Polymerization by Binding to the Colchicine Binding Site" *Bioorg. Med. Chem. Lett.*, vol. 4, No. 14, pp. 1725-1728 (1994).

Huber, et al., "Tubulin Binding of Conformationally Restricted Bis-Aryl Compounds", *Bioorg. Med. Chem. Lett,*, vol. 1, No. 5, pp. 243-246 (1991).

Josefsson, et al., "Suppression of Type II Collagen-Induced Arthritis by the Endogenous Estrogen Metabolite 2-Methoxyestradiol", *Arthristis & Rheumatism*, vol. 40, No. 1, pp. 154-163 (Jan. 1997).

Kabarity, et al., "Further Investigations on the cytological effects of some contraceptives" Mutation Research, vol. 135, pp. 181-188 (1984).

Kelly, et al., "The Stimulation of Prostaglandin Production by Two Antiprogesterone Steriods in Human Endometrial Cells" *J. Clin. Endocrinol Metab.*, vol. 62, No. 6, pp. 1116-1123 (Jun. 1986) (Abstract only).

Klauber, et al., "Inhibition of Angiogenesis and Breast Cancer in Mice by the Microtubule Inhibitors 2-Methoxyestradiol and Taxol", *Cancer Research*, vol. 57, pp. 81-86 (Jan. 1, 1997).

Le Bras, J. et al. "Activation and Regioselective Ortho-Functionalzation of the A-Ring and β-Estradiol Promoted by "Cp*Ir": An Efficient Organometallic Procedure for the Synthesis of 2-Methoxyestradiol", *Organometallics*, vol. 16, pp. 1765-1771 (1997).

Lilopristone/ 1-[4-(Dimethylamino)phenyl]-17-hydroxy-17-(3-hydroxy-1-propenyl) estra-4, 9-dien-3-one; ZK 98734; *Dictionary of Drugs*, (1990), *Dictionary of Steriods*, (1991), *Dictionary of Organic Compounds* (6th Ed. 1996), *Dictionary of Pharmacological Agents* (1997) (Identifier Only).

Lin et al., "Interactions of Tubulin with Potent Natural and Synthetic Analogs of the Antimitotic Agent Combretastatin: a Structure—Activity Study", *Molecular Pharmacology*, vol. 34, No. 2, pp. 200-208 (Aug. 1988).

Lincoln et al., "Conformation of Thiocolchicine and Two B-Ring-Modified Analogues Bounds to Tubulin Studied with Optical Spectroscopy", *Biochemsitry*, vol. 30, No. 5, pp. 1179-1187 (1991).

Lottering et al., "Effects of 17β—Extradiol Metabolites on Cell Cycle Events in MCF—7 Cells", *Cancer Research*, vol. 52, pp. 5926-5932 (Nov. 1, 1992).

Lottering, et al., "17β-Estradiol Metabolies Affect Some Regulators of the MCF-7 Cell Cycle", *Cancer Letters*, vol. 110, pp. 181-186 (1996).

Meikrantz, et al., "Apoptosis and the Cell Cycle", *J. of Cellular Biochem.* vol. 58, pp. 160-174 (1995).

Miller, et al., "Synthesis and Structure-Activity Profiles of A-Homoestranes, the Estratropones", *J. Med. Chem.*, vol. 40, pp. 3836-3841 (1997).

Miller, Thomas Allen "Tubulin as a Therapeutic Target", *DAI-B*, vol. 59, No. 7, p. 3454 (Jan. 1999) (Abstract Only).

Morgan, et al., "Calcium and Oestrogen Interactions upon the Rat Thymic Lymphocyte Plasma Membrane", *Biochemical and Biophysical Research Communications*, vol. 72, No. 2, pp. 663-672 (Sep. 20, 1976).

Mukhopadhyay, et al. "Induction of Apoptosis in Human Lung Cancer Cells after Wild-Type p53 Activation by Methoxyestadiol", *Oncogene*, vol. 14, pp. 379-384 (1997).

Mukundan et al., "Liver Regenration in Oral Contraceptive Treated Female Rats—Effects of Moderate Malnutrition", *Hormone and Metabolic Research*, vol. 16, pp. 641-645 (Dec. 1984).

Nakamura et al., "Studies on the Total Synthesis of dl-Colchiceine. I. Synthesis of 3-Hydroxy-9, 10, 11-trimethoxy-1,2,3,4,6,7-hexahydro-5H-dibenzo[a,c]cycloheptatrien-5-one", *Chem. Pharm. Bull.*, vol. 10, pp. 281-290 (1962).

Nakagawa-Yagi, et al., "The Endogenous Estrogen Metabolite 2-Methoxyestradiol Induces Apoptotic Neuronal Cell Death *In Vitro*", *Life Sciences*, vol. 58, No. 17, pp. 1461-1467 (1996).

Sawada et al., "Colchicine-Like Effect of Diethylstilbestrol (DES) on Mammalian Cells in Vitro", *Mutation Research*, vol. 57, pp. 175-182 (1978).

Seegers, J. C. et al., "The Cytotoxic Effects of Estradiol-17β, Catecholestradiols and Methoxyestradiols on Dividing MCF-7 and HeLa Cells", *J. Steroid Biochem*, vol. 32, No. 6, pp. 797-809 (1989).

Sharp et al., "Diethylstilboestrol: the Binding and Effects of Diethylstilboestrol upon the Polymerisation and Depolymerisation of Purified Microtubule Protein *in vitro*", *Carcinogenes*, vol. 6, No. 6, pp. 865-871 (1985).

Spicer et al., "Catecholestrogens Inhibit Proliferation and DNA Synthesis of Porcine Granulosa Cells in Vitro: Comparison with Estradiol, 5α-dihydrotestosterone, Gonadotropins and Catecholamines", *Molecular and Cellular Endocrinology*, vol. 64, pp. 119-126 (1989).

Sternlicht et al., "Colchicine Inhibition of Microtubule Assembly via Copolymer Formation", *The Journal of Biological Chemistry*, vol. 254, No. 20, pp. 10540-10550 (1979).

Sun et al., "Antitumor Agents. 139. Synthesis and Biological Evaluation of Thiocolchicine Analogs 5, 6-Dihydro-6(S)-(acyloxy)- and 5,6-Dihydro-6(S)-[(acyloxy)methyl]-1,2,3-trimethoxy-9-(methylthio)-8H-cyclohepta[a]naphthalene-8-ones as Novel Cytotoxic and Antimitotic Agents.", *J. Med. Chem.*, vol. 36, pp. 544-551 (1993).

Sunagawa et al., "Synthesis of Colchicine; Synthesis of dl-Demethyoxydeoxy-hexahydrocolchicine", *Chem. Pharm. Bull.*, vol. 9, pp. 81-83 (1961).

Teranishi, Masonori, et al., "Methylation of Catechol Estrogen with Diazomethane", *Chem. Pharm. Bull.*, vol. 31, No. 9, pp. 3309-3314 (1983).

Tishler, et al., "Microtubule-Active Drugs Taxol, Vinblastine, and Nocodazole Increase the Levels of Transcriptionally Active p53", *Cancer Research*, vol. 55, pp. 6021-6025 (Dec. 15, 1995).

Tsutsui et al., "Comparison of Human Versus Syrian Hamster Cells in Culture for Induction of Mitotic Inhibition, Binucleation and Multinucleation, Following Treatment with Four Aneuploidogens", *Toxic in Vitro*, vol. 4, No. 1, pp. 75-84 (1990).

Utne, T., et al., "The Synthesis of 2-and 4-Fluoroestadiol", *Journal of Organic Chemistry*, vol. 33, No. 6, pp. 2469-2473 (Jun. 1968).

Van Geerestein, et al. Structure of 11.beta.-(4-(dimethylamino)phenyl)-17.beta.-hydroxy-17.alpha.-(2-propenyl) e stra-4,9-dien-3-one, *Acta Crystall Ogr., Sect. C: Cryst. Struct. Commun.*, vol. C43, No. 2, pp. 319-322 (1987) (Identifier Only).

Van Tamelen et al., "The Synthesis of Colchicine", *Tetrahedron*, vol. 14, p. 8-34 (1961).

Wang, Zhiqiang, et al., "An Optimized Synthesis of 2-Methosyestradiol, a Naturally Occurring Human Metabolite with Anticancer Activity" *Synth. Commun.* vol. 28, No. 23, pp. 4431-4437 (1998).

Wheeler, W.J. et al., "Mitotic Inhibition and Aneuploidy Induction by Naturally Occurring and Synthetic Estrogens in Chinese Hamster Cells in Vitro", *Mutation Research*, vol. 171, pp. 31-41 (1986).

Wheeler, W.J. et al., "Mitotic Inhibition and Chromosome Displacement Induced by Estradiol in Chinese Hamsters Cells", *Cell Motility and the Cytoskeleton*, vol. 7, No. 3, pp. 235-247 (1987).

Yue, et al., "2-Methoxydestradiol, an Endogenous Estrogen Metabolite, Induces Apoptosis in Endothelial Cells and Inhibits Angiogenesis: Possible Role for Stress-Activated Protein Kinase Signaling Pathway and Fas Expression", *Molecular Pharm.* vol. 51, pp. 951-962 (1997).

Guangrong, et al., "Effect of Components of Crown Ether Copper(I)Iodide Mixed Catalyst on Nucleophilic Substitution of Bromoestrogen" *Chemical Abstracts*, vol. 111, No. 21, Abstract No. 195225, p. 818, col. 1, (Nov. 20, 1989).

The Merck Index, 11th Edition, paragraphs 583-584, pp. 88(1989).

Ochs, et al., "Effect of Tumor Promoting Contraceptive Steriods on Growth and Drug Metabolizing Enzymes in Rat Liver", *Cancer Res.*, vol. 46, No. 3, pp. 1224-1232 (1986) (Abstract).

Mayol, et al., "Ethynylestradiol- Induced Cell Proliferation in Rat Liver Involvement of Specific Populations of Hepatocytes", *Carcinogenesis*, vol. 12, No. 12, pp. 2381-2388 (1992) (Abstract).

*Research Plus Catalog*, pp. 50-58, 1993.

News Article: Hoffman-La Roche Signs $70 Million Deal with Millenium on Genomics Technology, *Genetic Engineering News*, Apr. 15, 1994.

News Article: Advanced Drug Delivery Systems Peak Interest of Pharmaceutical & Biotech Firms, *Genetic Engineering News*, Apr. 15, 1994.

News Article: Nasal Spray for Treating Bleeding Disorders, *Genetic Engineering News*, Apr. 15, 1994.

Aboulwafa et al., Synthesis and evaluation for uterotrophic and antiimplantation activities of 2-substituted estradiol derivatives, *Steroids*, vol./Iss: 57, pp. 199-204, Apr. 1992.

Algire, G.H. et al., Vascular reactions of normal and malignant tumors in vivo. 1. Vascular reactions of mice to wounds and to normal and neoplastic transplants, *Journal of the National Cancer Institute*, vol./Iss: 6, pp. 73-85 Aug. 1945.

Aliev et al., 54929q Synthesis of cycloalkyl derivatives of dihydric phenols and their ethers, *Chemical Abstracts*, vol./Iss: 72, p. 370, 1970.

Anstead et al., The Estradiol Pharmacophore: Ligand Structure-Estrogen Receptor Binding Affinity Relationships and a Model for the Receptor Binding Site, *Steroids*, vol./Iss: 62, pp. 268-303, 1997.

Arnoldi et al., Sweet Isovanillyl Derivatives: Synthesis and Structure-Taste Relationships of Conformationally Restricted Analogs (Abstract only), *Journal of Agric. Food Chem.*, vol./Iss: 46(10), pp. 4002-4010, 1998.

Attalla et al., 2-Methoxyestradiol-Induced Phosphorylation of Bcl-2: Uncoupling from JNK/SAPK Activation (Abstract only), *Biochemical and Biophysical Research Communications*, vol./Iss: 247(3), pp. 616-619, Jun. 29, 1998.

Barnes et al., Tumor Necrosis Factor Production in Patients with Leprosy, *Infection and Immunity*, vol./Iss:60(4), pp. 1441-1446, Apr. 1992.

Bindra et al., Studies in Antifertility Agents.8.Seco Steroids: 2. 5,6-Secoestradiol and Some Related Compounds, *Journal of Medicinal Chemistry*, vol./Iss: 18(9), pp. 921-925, 1975.

Blickenstaff et al., Synthesis of Some Analogs δ Estradiol, *Steroids*, vol./Iss: 46(4,5), pp. 889-902, Oct. 1985.

Boyce et al., Some Preliminary Synthetical Studies with 5,6,7,8-Tetra-hydro-8-methylindane-1,5-dione, *Unknown*, pp. 4547-4553, 1960.

Brandi et al., Bone endothelial cells as estrogen targets, (Abstract only) *Calcif. Tissue Int.*, vol./Iss: 53(5), pp. 312-317, 1993.

Brem, H. et al., Interstitial chemotherapy with drug polymer implants for the treatment of recurrent gliomas, *Journal of Neurosurgery*, vol./Iss: 74, pp. 441-446, Mar. 1, 1991.

Burrows, N.P., Thalidomide Modifies Disease, *British Medical Journal*, vol./Iss:307, (6909) pp. 939-940, Oct. 9, 1993.

Cambie et al., Aromatic Steroids. Part II. Chromium Trioxide Oxidation of Some Oestra-1,3-5(10)-trienes, *Journal of the Chemical Society*, vol./Iss:9, pp. 1234-1240, 1969.

Cambie et al., Aromatic Steroids. Part I. Oxidation Products of 3-Methoxyestra-1,3,5(10-triene- 17βyl Acetate *J. Chem. Soc.*, pp. 2603-2608, 1968.

Corey et al., Applications of N,N-Dimethythydrazones to Synthesis. Use in Efficient, Positionally and Steroechemically Selective C-C Bond Formation; Oxidative Hydrolysis to Carbonyl Compounds, *Tetrahedron, Letters* vol./Iss: 1, pp. 3-6, 1976.

Corey et al., Facile Conversion of N,N-Dimethylhydrazones to Cabonyl Compounds by Cupric Ion-Catalyzed Hydrolysis, *Tetrahedron Letters*, vol./Iss: 41, pp. 3678-3668, 1976.

Crabbe, P., Cotton effect of the styrene chromophore, (Abstract only) *Chem. Ind.*, vol./Iss: 27, pp. 917-918, 1969.

D'Amato, R.J. et al., Thalidomide is an Inhibitor of Angiogenesis, *Proceedings of the National Academy of Science USA*, vol./Iss: 91, pp. 4082-4085, Apr. 1, 1994.

Ding et al., Sex Hormone-Binding Globulin Mediates Prostate Androgen Receptor Action via a Novel Signaling Pathway, (Abstract only) *Endocrinology*, vol./Iss: 139(1), pp. 213-218, 1998.

Durani et al., Seco-Oestradiols and Some Non-Steroidal Oestsrogens: Structural Correlates of Oestrogenic Action, *Journal of Steroid Biochemistry*, vol./Iss: 11, pp. 67-77, 1979.

Eder et al., Synthese von Ostradiol (in German—No translation available) (English Abstract only), *Chem. Ber.*, vol./Iss: 109, pp. 2948-2953, 1976.

El-Tombary, Synthesis, Uterotropic, And Antiuterotrophic Activities foSome Estradiol Derivatives Containing Thiadiazole, Thiazoline, ad Thiazolidinone Moieties, *Arch. Pharm. Pharm. Med. Chem.*, vol./Iss: 330(9-10), pp. 295-302, 1997.

Emons et al., Modulation der hypophysaren Sekretion von Luteinisierendem Hormon (LH) durch Ostrogene, *Focus MHL*, vol./Iss: 3, pp. 221-228, 1986

Enjyoji, K. et al., Effect of Heparin on the Inhibition of Factor Xa by Tissue Factor Pathway Inhibitor: A Segment, $Gly^{237}$-$Phe^{243}$, of the third Kunitz Domain is a Heparin-Binding Site, *Biochemistry*, vol./Iss: 34(17), pp. 5725-5735, 1995.

Fanchenko et al., Characterisitics of the guinea pig uterus estrogen receptor system (Abstract only), *Byull. Eksp. Biol. Med.*, vol./Iss: 85(4), pp. 467-470, 1978.

Fetizon et al., Synthesis of 2-keto steroids (Abstract only), *Bull. Soc. Chim. FR.*, vol./Iss: 8, pp. 3301-3306, 1968.

Fevig et al., A Short, Stereoselective Route to 16α(Substituted-alkyl)estradiol Derivatives, *Journal of Organic Chemistry*, vol./Iss: 52, pp. 247-251, 1987.

Field et al., Effect of Thalidomide on the Graft versus Host Reaction, *Nature*, vol./Iss:211 (5055), pp. 1308-1310, Sep. 17, 1966.

Fieser et al., N-Methylformanilide, *Organic Synthesis Collective vol. 3*, vol./Iss: 3, pp. 590-591, 1955.

Flohe et al., Studies on the Hypothetical Relationship of Thalidomide-induced Embryopathy and Collagen Biosynthesis *Arzneimitte/Forschung (Germany West)* vol./Iss: 31(2) pp. 315-320 Jan. 1, 1981.

Folkman et al., Angiogenesis Inhibition and Tumor Regression Caused by Heparin or a Heparin Fragment in the Presence of Cortisone, *Science*, vol./Iss: 221, pp. 719-725 Aug. 19, 1983.

Folkman, J., Tumor Angiogenesis: Therapeutic Implications, *New England Journal of Medicine*, vol./Iss: 285 (21), pp. 1182-1186, Nov. 18, 1971.

Folkman, J., et al. Induction of Angiogenesis During the Transition from Hyperplasia to Neoplasia, *Nature*, vol./Iss:339, pp. 58-61, May 4, 1989.

Folkman, J. et al., Tumor Behavior in Isolated Perfused Organs in vitro Growth and Metastases of Biopsy Material in Rabbit Thyroid and Canine Intestinal Segment, *Annals of Surgery*, vol/Iss: 164(3), pp. 491-502, Sep. 1, 1966.

Gadosy et al., Generation, Characterization, and Deprotonation of Phenol Radical Cations, *Journal of Physical Chemistry*, vol./Iss: 103, pp. 8834-8839, 1999.

Gandhi et al., Mannich Reaction of Estrone (Abstract Only), *Journal of Indian Chem. Soc.*, vol./Iss: 39, pp. 306-308, 1962.

Gaslini et al., Reaction of Eugenol with Synthesis Gas. Synthesis of 5,6,7,8-Tetrahydro-3-methoxy-2-napthol (Abstract Only) *document illegible Journal of Organic Chemistry*, vol/Iss:29(5), pp. 1177-1180, May 1964.

Gian Tondury et al., Zur Wirkung Der Sexualhormone Auf Wachstum und Differenzierung (See English Summary p. 55), *Cambridge Philosophical Society*, pp. 28-58, Dec. 17, 1955.

Gimbrone, M.A. et al., Tumor Growth and Neovascularization: An Experimental Model Using the Rabbit Cornea, *Journal of the National Cancer Institute*, vol./Iss: 52(2), pp. 413-427, Feb. 1974.

Gimbrone, M.A. et al., Tumor dormancy in vivo by Prevention of Neovascularization, *Journal of Experimental Medicine*, vol./Iss: 136, pp. 261-276, 1972.

Gonzalez et al., Synthesis and Pharmacological Evaluation of 8αEstradiol Derivatives, *Steroids*, vol./Iss: 40(2), pp. 171-187, Sep. 1982.

Gross, J.L. et al., Modulation of Solid Tumor Growth in vivo by bFGF (Abstract only), *Proceedings of the American*

*Association of Cancer Research,* vol./Iss: 31, pp. 79, Mar. 1990.

Gujjar et al., The Effect of Estradiol on Candida albicans Growth, *Annals of Clinical and Laboratory Science,* vol./Iss: 27(2), pp. 151-156, 1997.

Gunzler, V., Thalidomide-A Therapy for the Immunological Consequences of HIV Infection?, *Medical Hypothesis,* vol./Iss: 30(2), pp. 105-109, Oct. 1989.

Gupta et al., Antifertility Agents. XIV. Secosteroids. VII. Synthesis of 2α and 2β, 6β-dimethyl-3β-(p-hyroxyphenyl)-trans-bicyclo[4.3.0]nonan-7-ones and some related compounds (Abstract only), *Indian Journal of Chemistry,* vol./Iss: 13(7), pp. 759-760, 1975.

Gupta et al., Studies in Antifertility Agents. Part XVIII. 2α6β-Diethyl-3β-(p-hydroxyphenyl)-trans-bicyclo[4.3.0]nonan-7β-ol and 6β-methyl-3β-(p-hydroxyphenyl)-2α-propyl-trans-bicyclo[4.3.0]nonan-7β-ol (Abstract only), *Indian Journal of Chemistry,* vol./Iss:19B(10), pp. 886-890, 1980.

Gutierrez-Rodriguez et al., Treatment of Refractory Rheumoid Arthritis—The Thalidomide Experience *The Journal of Rheumatology,* vol./Iss: 16(2), pp. 158-163, Feb. 1989.

Gutierrez-Rodriguez, O., Thalidomide—A Promising New Treatment for Rheumatoid Arthritis, *Arthritis and Rheumatism,* vol./Iss: 27(10), pp. 1118-1121, Oct. 1984.

Hahnel et al., The Specificity of the Estrogen Receptor of Human Uterus, *Journal of Steroid Biochemistry,* vol./Iss: 4, pp. 21-31, 1973.

Handley et al., Chronic bullous disease of childhood and ulcerative colitis, *British Journal of Dermatology,* vol./Iss: 127(40), pp. 67-68, Jul. 1, 1992.

He et al., Novel Cytokine Release Inhibitors. PartII Steroids, *Bioorganic & Medicinal Chemistry Letters,* vol./Iss: 8, pp. 2825-2828, 1998.

Hejaz et al., Synthesis and Biological Activity of the Superstrogen (E)-17-Oximino-3-O-sulfamoyl-1,3,5(10)-estratriene: X-ray Crystal Structure of (E)-17-Oximino-3-hydroxy-1,3,5(10)-estratriene, *Journal of Medical Chemistry* vol./Iss: 42(16), pp. 3188-3192, 1999.

Heney et al., Thalidomide treatment for chronic graft-versus-host disease, *British Journal of Haematology,* vol./Iss: 78(1), pp. 23-27, May 1991.

Holker et al., The Reactions of Estrogens with Benzeneseleninic Anhydride and Hexamethyldisilazane, *J. Chem. Soc. Perkin Trans.,* vol./Iss: 1, pp. 1915-1918, 1982.

Hu, G., Neomycin Inhibits Angiogenin-induced Angiogenesis (Abstract Only), *Proceedings of the National Academy of Sciences, USA,* vol./Iss: 95 (17), pp. 9791-9795, 1998.

Ikegawa et al., Immunoaffinity extraction for liquid chromatographic determination of equilin and its metabolites in plasma (Abstract only), *Biomed. Chromatogr.,* vol./Iss: 10(2), pp. 73-77, 1996.

Imamura et al., Method for Manufacture of Dihydric Phenols (Abstract only), *USPATFULL 76:20259 US 3,950,437,* Apr. 13, 1976.

Ingber, D. et al., Synthetic analogues of fumagillin that inhibit angiogenesis and suppress tumor growth, *Nature,* vol./Iss: 348, pp. 555-557, Dec. 6, 1990.

Iriarte et al., Steroids (XCIV), Synthesis of 2-methyl and 1,2-dimethyl estrogens (Abstract only), *Tetrahedron,* vol./Iss: 3, pp. 28-36, 1958.

Jaggers et al., Potent Inhibitory Effects of Steroids in an in vitro Model of Angiogenesis (Abstract only), *Journal of Endocrinology,* vol./Iss: 150(3), pp. 457-464, 1996.

Jhingran et al., Studies in Antifertility Agents—Part XLI: Secosteroids-χ: Syntheses of Various Stereoisomers of(+=)-2,6β-diethyl-7α-ethynyl-3-(p-hydroxyphenyl)-trans-bicyclo[4.3.0)nonan-7β-ol., *Steroids,* vol./Iss: 42(6), pp. 627-634, 1983.

Karwat, Separation and Recovery of Hydrogen Sulfide from Hydrocarbon Mixture, *Caplus DE 1103310,* Sep. 2, 1959.

Kataoka et al., An Agent that Increases Tumor Suppressor Transgene Product Coupled with Systemic Transgene Delivery Inhibits Growth of Metastatic Lung Cancer in Vivo (Abstract only), *Cancer Research,* vol./Iss: 58(21) pp. 4761-4765, Nov. 1998.

Knighton, D. et al., Avascular and Vascular Phases of Tumour Growth in the Chick Embyo, *British Journal of Cancer,* vol./Iss: 35, pp. 347-356, 1977.

Kole et al., Studies in Antifertility Agents. 11. Secosteroids. 5.Synthesis of 9,11-Secoestradiol, *Journal of Medicinal Chemistry,* vol./Iss: 18(7), pp. 765-766, 1975.

Kovacs et al., Steroids. XXIII. Synthesis of 2- and 4-hydroxy and 2,4-dihydroxy derivatives of estrone and estradiol (Abstract only), *Acta Phys.Chem.,* vol./Iss: 19(3), pp. 287-290, 1973.

Laguchev, S.S., Hormonal Regulation of Cell-Divisions in the Mammary Gland, *Path.-Biol.,* vol./Iss: 9(5-6), pp. 638-640, Mar. 1961.

Lewis, Richard J., *Hawley's Condensed Chemical Dictionary,* pp. 577, Jan. 1993.

Lewis, Richard J., *Hawley's Condensed Chemical Dictionary,* pp. 128-129, Jan. 1993.

Li, J., et al., (DN 103:65176) Catechol Formation of Fluoro- and Bromo-substituted Estradiols by Hamster Liver Microsomes. Evidence for Dehalogenation. (Abstract only), *CAPLUS: Molecular Pharmacology,* vol./Iss: 27(5), pp. 559-565, 1985.

Lien, W. et al., The blood supply of experimental liver metastases. II. A Microcirculatory study of the normal and tumor vessels of the liver with the use of perfused silicone rubber, *Surgery,* vol./Iss: 68(2), pp. 334-340, Aug. 1970.

Limantsev et al. Effect of some estrogen structural analogs on the development of the mouse embyo (Abstract only) *Akush Jinekol.* vol./Iss: 6 pp. 55-56 Date: 1982.

Liu et al. Total Synthesis of (+=)-$\Delta^{9(12)}$-Capnellene *Tetrahedron Letters* vol./Iss: 26 (40) pp. 4847-4850 Date: 1985.

Loozen et al. An approach to the synthesis of 7.beta.-amino estrogens (Abstract only) *Recl.: J.R. Neth.Chem. Soc.* vol./Iss: 102(10) pp. 433-437 Date: 1983.

Lovely et al. 2-(Hydroxyalkyl)estradiols: Synthesis and Biological Evaluation *Journal of Medicinal Chemistry* vol./Iss: 39 pp. 1917-1923 Date: 1996.

Maro et al. Mechanism of Polar Body Formation in the Mouse Oocyte: An Interaction Between the Chromosomes, the Cytoskeleton and the Plasma Membrane *Journal of Embryology and Experimental Morphology* vol./Iss: 92 pp. 11-32 Date: 1986.

Meza et al. Managing the Gastrointestinal Complications of AIDS *Drug Therapy* vol./Iss: 23 (11) pp. 74-83 Date: Nov. 1993.

Michel et al. Inhibition of synaptosomal high-affinity uptake of dopamine and serotonin by estrogen agonists and antagonists (Abstract only) *Biochem. Pharmacol.* vol./Iss: 36(19) pp. 3175-3180 Date: 1987.

Morisaki et al., Steroids, L1. Aromatization reaction of the cross-conjugated dienone system by Zinc 9. (Abstract only), *Chem. Pharm. Bull.*, vol/Iss: 14(8), pp. 866-872, 1966.

Naafs et al., Thalidomide Therapy An Open Trial, *International Journal of Dermatology*, vol./Iss: 24 (2), pp. 131-134, Mar. 1985.

Nambara et al., Microbial transformation products derived from steriods. I. Synthesis of 1,2- and 3-dimethoxy-4-methylestratrienes (Abstract only), *Chem. Pharm. Bull.*, vol./Iss: 20(2), pp. 336-342, 1972.

Nambara et al., Synthesis of 16β-Oxygenated Catechol Estrogen Methyl Ethers, New and Potential Metabolites, *Chemical & Pharmaceutical Bulletin*, vol./Iss: 23(7), pp. 1613-1616, Jul. 1975.

Nambara, T., et al., DN 82:43650; Analytical Chemical Studies on Steroids. LXXIII. Synthesis of Epimeric 2-Hydroxy-16-Chlorestrong Monomethyl Ethers (Abstract only), *HCAPLUS-Chemical and Pharmaceutical Bulletin*, vol./Iss: 22(10), pp. 2455-2457, 1974.

Newkome et al., Synthesis of Simple Hydrazones of Carbonyl Compounds by an Exhange Reaction, *Journal of Organic Chemisty*, vol./Iss: 31, pp. 677-681, Mar. 1966.

Nguyen, M. et al., Elevated Levels of the Angiogenic Peptide Basic Fibroblast Growth Factor in Urine of Bladder Cancer Patients, *Journal of the National Cancer Institute*, vol./Iss: 85 (3), pp. 241-242, Feb. 3, 1993.

Numazawa et al., Novel and Regiospecific Synthesis of 2-Amino Estrogens via Zincke Nitration, *Steroids*, vol./Iss: 41(5), pp. 675-682, 1983.

Omar et al., Synthesis, binding affinities and uterotrophic activity of some 2-substituted estradiol and ring-A-fused pyrone derivatives, *European Journal of Medicinal Chemistry*, vol./Iss: 29, pp. 25-32, 1994.

Pert et al., Preparations of 2,4-disubstituted estradiols (Abstract only), *Australian Journal of Chemistry*, vol./Iss: 42(3), pp. 421-432, 1989.

Peters et al., 17-Desoxy Estrogen Analogues, *Journal of Medicinal Chemistry*, vol./Iss: 32(7), pp. 1642-1652, 1989.

Pfeiffer et al., Are catechol estrogens obligatory mediators of estrogen action in the central nervous system? I. Characterization of pharmacological probes with different receptor binding affinities and catechol estrogen formation rates (Abstract only), *Journal of Endocrinology*, vol./Iss: 110(3), pp. 489-497, 1986.

Plum et al., Vaccination with Peptide to the Heparin Binding Domain of bFGF Conjugated to Liposomes Inhibits bFGF Induced Neovascularization (Abstract only), *Proceedings of the American Association for Cancer Research Annual.*, vol./Iss: 39, p. 8, Mar. 1998.

Powell et al., Investigation and Treatment of Orogenital Ulceration; studies on a Possible Mode of Action of Thalidomide, *British Journal of Dermatology*, vol./Iss: 113, Supp. 28, pp. 141-144, Jul. 1985.

Romanelli et al., Ethyl-p-Dimethylaminophenylacetate, *Organic Synthesis*, vol./Iss: 5, p. 552, Oct. 24, 1973.

Sakakibara, Kyoichi, 2-Hydroxy-1,3,5(10)-estratriene derivatives (Abstract only) (Identifier: XP-002186126), *Chemical Abstracts*, vol./Iss: 60(1), Jan. 6, 1964.

Sato et al., Natural estrogens induce modulation of microtubules in Chinese hamster V79 cells in culture (Abstract only), *Horm. Carcinog. II. Proceedings Int. Symp., 2nd (1996), Meeting Date 1994*, pp. 454-457, 1996.

Seaver, Sally, Monoclonal Antibodies in Industry: More Difficult than Originally Thought, *Genetic Engineering News*, vol./Iss: 14, pp. 10 and 21, Aug. 1994.

Seegers et al., Cyclic-AMP and Cyclic-GMP Production in MCF-7 Cells Exposed to Estradiol-17 Beta, Catecholestrogens and Methoxy-Estrogens in MCF-7 Cells (Meeting Abstract only), *Joint MCI-1st Symposium, Third 1st International Symposium, Biology and Therapy of Breast Cancer*, Sep. 25, 1989.

Seegers et al., The Mammalian Metabolite, 2-methoxyestradiol, Affects P53 Levels and Apoptosis Induction in Transformed Cells but Not in Normal Cells (Abstract only), *Journal of Steroid Biochemistry and Molecular Biology*, vol./Iss: 62(4), pp. 253-267, Jul. 1997.

Shah et al., (+/=)-(N-alkylamino)benzazepine Analogs: Novel Dopamine D1 Receptor Antagonists (Abstract only), *Journal of Medicinal Chemistry*, vol./Iss: 38(21), pp. 4284-4293, Oct. 13, 1995.

Shishkina et al., Synthesis and properties of condensed heterocyclic derivatives of estra-4, 9-dien-17.beta.-ol-3-one (Abstract only), *Khim.-Farm.Zh.*, vol./Iss: 8(1), pp. 7-11, 1974.

Sidky et al., Inhibition of Angiogenesis by Interferons: Effects on Tumor- and Lymphocyte-induced Vascular Repsonses, *Cancer Research*, vol./Iss: 47, pp. 5155-5161, Oct. 1, 1987.

Siracusa et al., The Effect of Microtubule- and Microfilament-disruptiing Drugs α Preimplantation Mouse Embryos (abstract Only), *Jouranl of Embryology and Experimental Morphology*, vol./Iss:60, pp. 71-82, Dec. 1980.

Soker et al., Neuropilin-1 is Expressed by Endothelial and Tumor Cells as an Isoform-Specific Receptor for Vascular Endothelial Growth Factor, *Cell*, vol./Iss: 92, pp. 735-745, Mar. 20, 1998.

Spyriounis et al., Copper (II) complex of an estradiol derivative with potent antiinflammatory properties (Abstract only), *Arch. Pharm.*, vol./Iss: 324(9), pp. 533-536, 1991.

Srivastava, A. et al., The Prognostic Significance of Tumor Vascularity in Intermediate-Thickness (0.76-4.0mm Thick), Skin Melanoma, *American Journal of Pathology*, vol./Iss: 133(2), pp. 419-424, Nov. 1988.

Staples et al., Structural Requirements for Steroid Inhibition of Sheep Lymphocyte Mitogenesis in vitro, *Steroids*, vol./Iss: 44(5), pp. 419-433, Nov. 1984.

Starkov et al., Mono- and Dialkylation of Guaiacol by Olefins on KU-2 Cation Exchanger (Abstract only), *Zhumal Prikladnoi Khimii*, vol./Iss: 41(3), pp. 688-690, 1968.

Taylor, S. et al., Protamine is an Inhibitor of Angiogensis, *Nature*, vol./Iss: 297, pp. 307-312, May 27, 1982.

Tremblay et al., A Convenient Synthetic Method for Alpha-Alkylation of Steroidal 17-Ketone: Preparation of 16β-(THPO-Heptyl)-Estradiol, *Synthetic Communications*, vol./Iss: 25(16), pp. 2483-2495, 1995.

Tremblay et al., Synthesis of 16-(Bromoalkyl)-Estradiols Having Inhibitory Effect on Human Placental Estradiol 17β-Hydroxysteroid Dehydrogenase (17βHSD Type 1), *Bioorganic & Medicinal Chemistry*, vol./Iss: 3(5), pp. 505-523, 1995.

Vicente et al., In Vitro Activity of Thalidomide Against Mycobacterium avium Complex, *Archives of Internal Medicine*, vol./Iss: 153(4), p. 534, Feb. 22, 1993.

Wang et al., Photoaffinity Labeling δ Human Placental Etradiol 17.beta.-dehydrogenase with 2- And 4-azidoestrone, 2- and 4-azidoestradiol (abstract Only) *Shengwu Huaxue Zazhi*, vol./Iss: 8 (6), pp. 715-718, 1992.

Weidner, N. et al., Tumor angiogenesis: A New Significant and Independent Prognostic Indicator in Early-Stage Breast Carcinoma, *Journal of the National Cancer Institute,* vol./Iss: 84, pp. 1875-1887, Dec. 16, 1992.

Weidner, N. et al., Tumor Angiogenesis Correlates with Metastasis in Invasive Prostate Carcinoma, *American Journal of Pathology,* vol./Iss: 143(2), pp. 401-409, Aug. 1993.

Weidner, N. et al., Tumor Angiogenesis and Metastasis-Correlation in Invasive Breast Carcinoma, *New England Journal of Medicine,* vol./Iss: 324 (1), pp. 1-8, Jan. 3, 1991.

Welsch et al., Staphylostatic Activity of Some New Diphenols, Napthols, and Chalcones (Abstract only), *Experientia,* vol/Iss: 11, pp. 350-351, 1955.

White et al., Treatment of Pulmonary Hemangiomatosis with Recombinant Interferon Alfa-2a, *The New England Journal of Medicine,* vol./Iss: 32(18), pp. 1197-1200, May 4, 1989.

Wiese et al., Induction of the Estrogen Specific Mitogenic Response of MCF-7 Cells by Selected Analogues of Estradiol-17β:A 3D QSAR Study, *Journal of Medicinal Chemistry,* vol./Iss: 40, pp. 3659-3669, 1997.

Wurtz et al., Three-Dimensional Models of Estrogen Receptor Ligand Binding Domain Complexes Based on Related Crystal Structures and Mutational and Structure-Activity Relationship Data, *Journal of Medicinal Chemistry,* vol./Iss: 41, pp. 1803-1814, 1998.

Yasuda et al., Accelerated differentiation in seminiferous tubles of fetal mice prenatally exposed to ethinyl estradiol (Abstract only), *Anat. Embryol. (Berl.),* vol./Iss: 174(3), pp. 289-299, 1986.

* cited by examiner

FIG_2

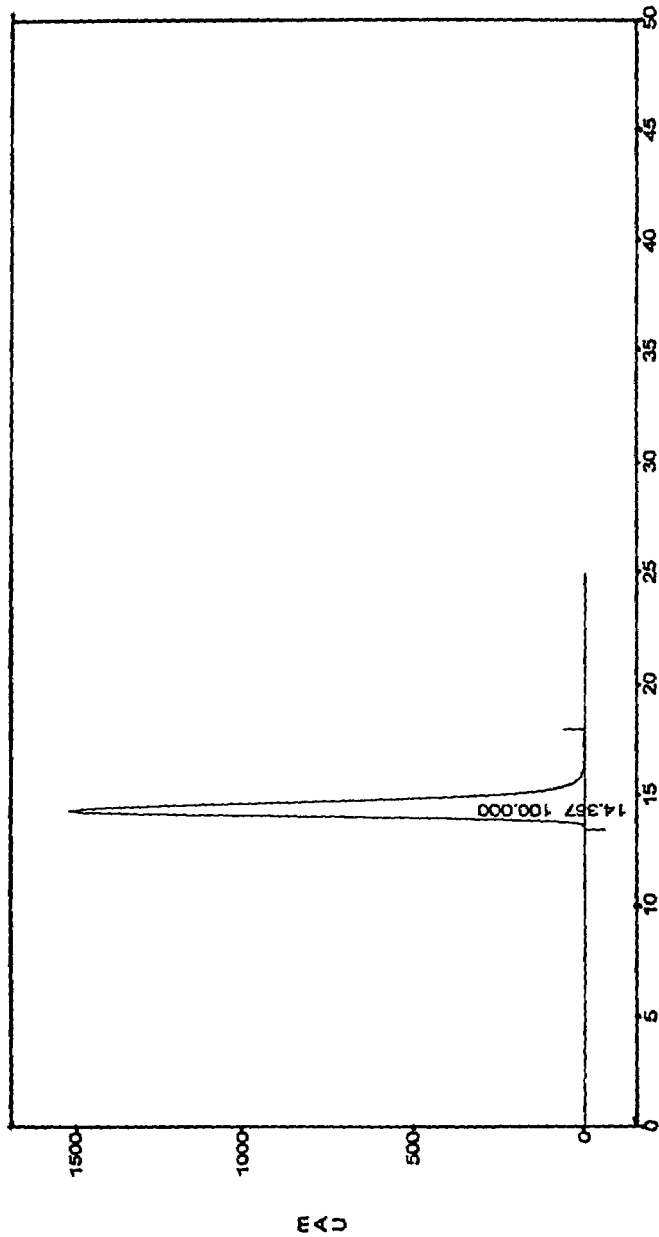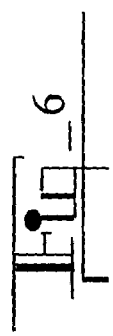
FIG. 6

Fig_7

FIG_9

FIG_10

Fig_11

Fig_12

FIG_14

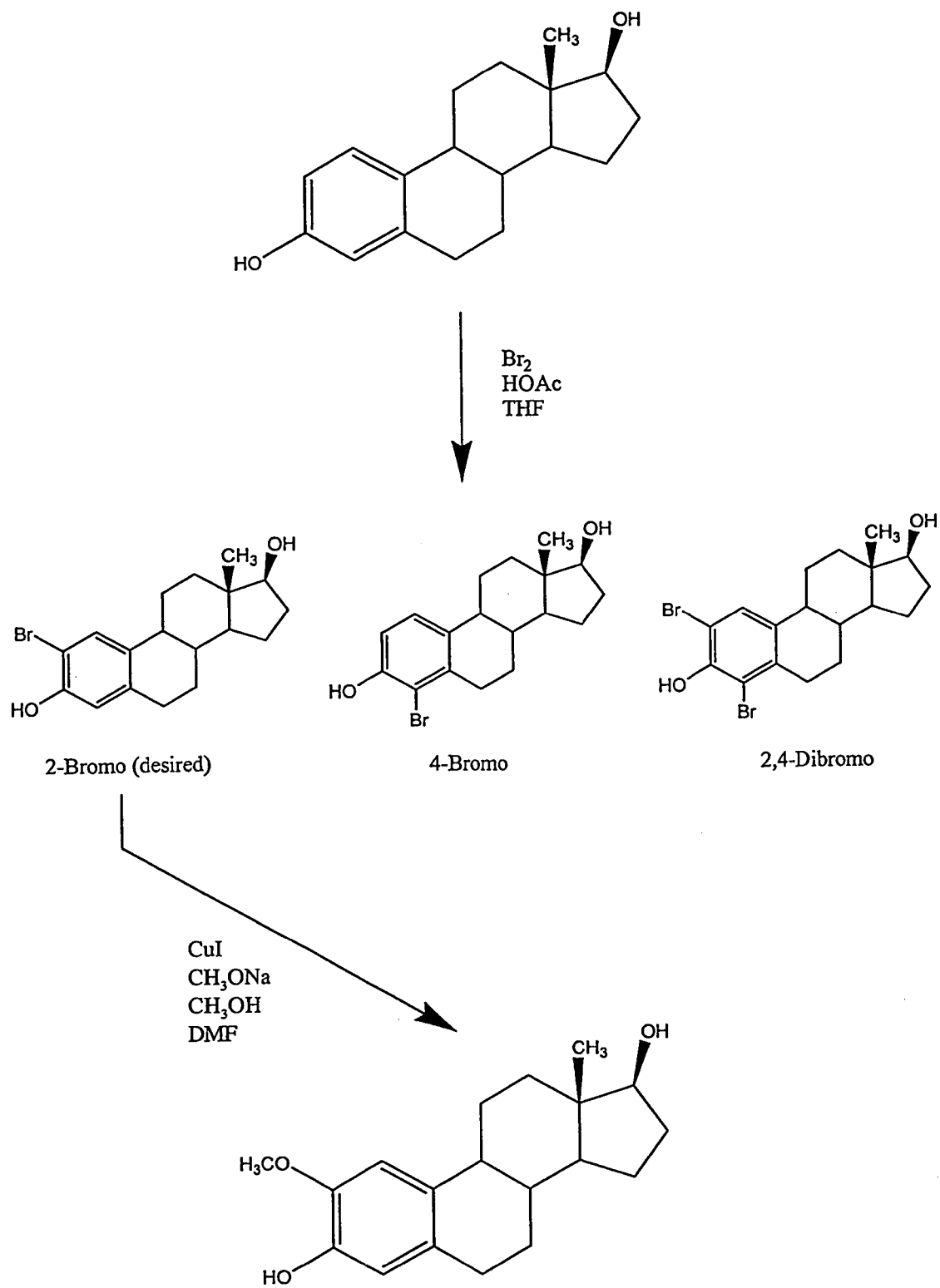
Fig_16

COMPOSITIONS COMPRISING PURIFIED 2-METHOXYESTRADIOL AND METHODS OF PRODUCING SAME

RELATED APPLICATIONS

This application claims priority to U.S. Provisional Application Ser. No. 60/150,293 filed Aug. 23, 1999.

FIELD OF THE INVENTION

The invention relates to the estradiol metabolite 2-methoxyestradiol and to methods of obtaining purified 2-methoxyestradiol.

BACKGROUND OF THE INVENTION

2-Methoxyestradiol, 1,3,5(10)-estratrien-2,3,17β-triol-2-methyl-ether (2-ME2) is an endogenous metabolite of estradiol, the major ovarian estrogen. The chemical formula of 2-ME2 is $C_{19}H_{26}O_3$, and the compound has a molecular weight of 302.4. 2-ME2 has low of estrogenic activity but has been found to have other biological effects.

U.S. Pat. Nos. 5,504,074, 5,661,143, and 5,892,069 to D'Amato et al. disclose methods of treating mammalian diseases characterized by abnormal cell mitosis using 2-ME2. Undesirable cell mitosis is characteristic of many diseases, including, but not limited to, cancer, atherosclerosis, proliferation of solid tumors, vascular malfunctions, endometriosis, retinopathies, arthropathies, and abnormal wound healing. In addition, cell mitosis is important in a wide variety of biological functions, including but not limited to the normal development of the embryo, formation of the corpus luteum, cyclic proliferation of uterine endometrium, wound healing, and inflammatory and immune responses.

U.S. Pat. No. 5,521,168 to Clark discloses using 2-ME2 for lowering intraocular pressure. 2-ME2 also inhibits estrogen-induced pituitary tumor angiogenesis and suppresses tumor growth in Fisher 344 rats as reported by Banerjee, S. K. et al., Proc. Amer. Assoc. Cancer Res. 39, March 1998.

Presently, commercially available preparations of 2-ME2 are either less than 98% pure or contain undesirable steroid contaminants that are of concern for pharmaceutical uses. Important contaminants of these preparations are estradiol, 4-hydroxyestradiol, 4-methoxyestradiol, 2-hydroxyestradiol, estrone, and 2-methoxyestrone. The amounts of these contaminants that are found in presently available 2-ME2 preparations are unacceptable for pharmaceutical applications.

Any therapeutic use of 2-ME2 in humans requires 2-ME2 having a high level of purity. In general, therapeutic agents are required to be substantially pure to avoid negative side effects of contaminants. In particular, since 2-ME2 has effects that are counteracted by estradiol and other estrogenic metabolites, it is crucial to have a 2-ME2 preparation substantially free of such contaminants. Effects that may be seen from contaminating estradiol, estrone, and 2-hydroxyestradiol include estrogenic effects such as feminization, endometrial proliferation, increased risk of uterine and breast cancer, developmental effects on sexual organs, inhibition of leukopoesis, and effects on hematopoetic cells. 4-hydroxyestradiol, 4-methoxyestradiol, and estradiol are known mutagens and carcinogens.

Accordingly, what is needed is a composition of 2-ME2 which is greater than 98% pure and which contains substantially no estradiol or other steroids having estrogenic or carcinogenic effects.

What is also needed is a composition containing 2-ME2 that is greater than 99.5% pure.

What is also needed are methods for making 2-ME2 of greater than 98% purity and containing substantially no estradiol or other steroids having estrogenic or carcinogenic effects.

Also needed are methods of substantially separating 2-ME2 from estradiol, related molecules, and other contaminants, resulting in 2-ME2 having a purity of greater than 99.5%.

SUMMARY OF THE INVENTION

The present invention provides 2-ME2 having greater than 98% purity, more preferably greater than 99% purity, most preferably greater than 99.5% purity. The 2-ME2 preparations preferably contain less than 0.03% estradiol, 0.02% or less 2-hydroxyestradiol, 0.02% or less 4-hydroxyestradiol, 0.02% or less 4-methoxyestradiol, and less than 0.02% estrone. More preferably, the 2-ME2 preparations contain 0.01% or less estradiol, 0.02% or less 2-hydroxyestradiol, 0.01% or less 4-hydroxyestradiol, 0.01% or less 4-methoxyestradiol, and 0.01% or less estrone.

The present invention also provides methods of obtaining 2-ME2 of greater than 98% purity, more preferably greater than 99% purity, most preferably greater than 99.5% purity. In some embodiments, the methods involve synthetic techniques. In other embodiments, the methods involve purification techniques to separate the 2-ME2 from other compounds. In yet other embodiments, the methods involve both synthetic techniques and purification techniques described herein.

The purification methods involve the use of liquid-solid chromatography (LSC) to separate 2-ME2 from other compounds. The chromatographic media is preferably silica. The solvent system comprises a non-polar solvent, such as chloroform, and a polar solvent, such as methanol.

Accordingly, an object of the present invention is to provide 2-ME2 having a purity greater than 98%.

Another object of the present invention is to provide 2-ME2 substantially free of estradiol, related compounds, and other unwanted impurities.

Still another object of the invention is to provide methods of obtaining substantially pure 2-ME2 by synthetic techniques.

Another object of the invention is to provide methods of obtaining substantially pure 2-ME2 by purification techniques.

Other features and advantages of the invention will be apparent from the following description of preferred embodiments thereof.

BRIEF DESCRIPTION OF THE DRAWINGS

FIG. 6 is a chromatogram of the 2-ME2 of the present invention produced in Example 2. The HPLC was run with a non-overloaded amount of sample, 75.6 µg (14 µl at 5.4 µl/ml).

FIG. 16 depicts a synthetic reaction scheme for the production of the 2-methoxyestradiol of the present invention, using estradiol as a starting material and employing bromination at the 2-position of the A ring of unblocked estradiol and reaction with methanol.

DETAILED DESCRIPTION OF THE INVENTION

The present invention is directed to 2-methoxyestradiol having a purity of greater than 98.0%, more preferably greater than 99.0%, and most preferably of 99.5% or higher. 2-ME2 can be obtained through synthesis methods or purification methods described herein that yield highly pure 2-ME2. The synthesis methods described herein may also be supplemented with the purification methods described herein to yield 2-ME2 having even greater purity.

Although the terms "2-methoxyestradiol" and 2-ME2 are specifically used herein, it should be understood that the methods disclosed herein can be used for synthesis or purification of other compounds, such as, but not limited to, estradiol and other structurally related steroids.

Methods of Synthesis

The present invention provides methods of synthesizing 2-ME2 to a purity of greater than 98.0%, more preferably greater than 99.0%, and most preferably of 99.5% or higher. The synthetic methods described herein can also be used, with minor modifications, to synthesize other 2- and 4-derivatives or analogues of estradiol, such as, for example, 4-methoxyestradiol and 4-hydroxyestradiol.

There are several synthetic approaches that can be taken to prepare 2-ME2 having a purity greater than 98.0%. Alternatively, 2-ME2 can be purified according to the following purification methods to have a purity greater than 98.0%. These different synthetic approaches utilize different starting materials and intermediates; consequently, different yields, side reactions and impurities will be obtained.

Figure 12:
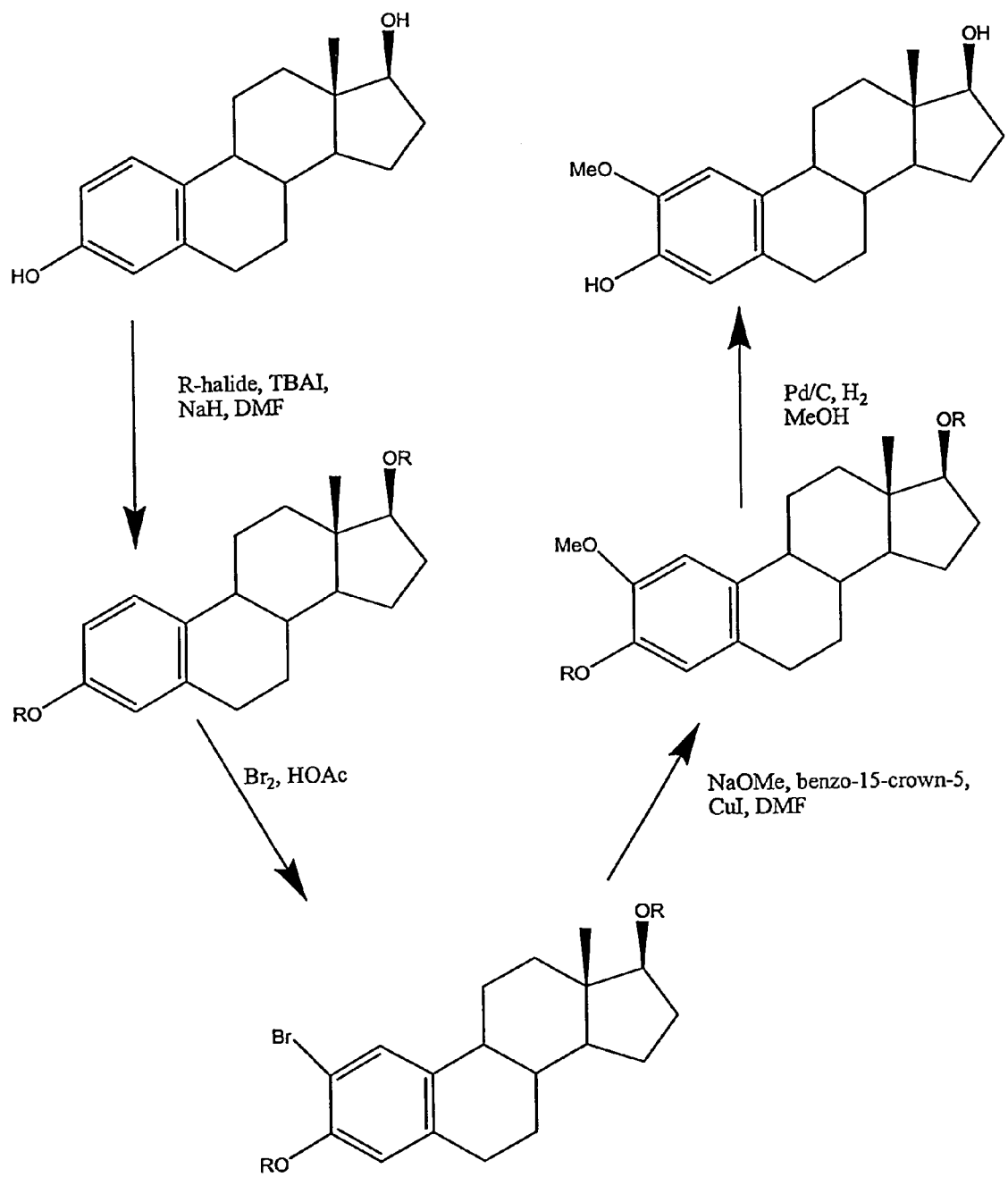
FIG. 12 depicts a synthetic reaction scheme for the production of the 2-methoxyestradiol of the present invention, using estradiol as a starting material and employing bromine, a crown ether, and a blocking group on the 3- and 17-position hydroxyloxygen atoms of the estradiol.

Two similar approaches employ estradiol as a starting material and utilize a brominated intermediate, as taught by Rao, P. N. et al., Synthesis, 1977, 168 and Chen, S-H et al., Steroids, 1986, 47, 63. The first approach is illustrated in FIG. 12. The free hydroxyl groups of estradiol are protected with a blocking group. A wide range of blocking groups can be used in the present invention. These blocking groups include, but are not limited to, alkyl, aryl, aralkyl groups, and alkyl, aryl, and aralkyl group containing one or more heteroatoms. For example, protection can be accomplished using an alkyl halide, such as benzyl bromide, to form an alkyl ether. Appropriate conditions for hydroxyl protection include reaction of the estradiol and alkyl halide in the presence of NaH and TBAI, optionally in the presence of a solvent, such as dimethyl formamide (DMF). The protected estradiol is then reacted with bromine, for example, in the presence of acetic acid. Protection of the free hydroxyls during bromination gives a higher yield of the 2-brominated intermediate (about 70% vs. about 20% without the protecting groups) (see Cushman, M. et al., J. Med. Chem. 1997, 40, 2323).

The bromine is then replaced with a methoxide group using a copper catalyst. For example, the brominated intermediate can be reacted with NaOMe in the presence of a copper catalyst, such as CuI. The reaction is preferably conducted in a solvent, such as DMF, optionally in the presence of a promoter. Acceptable promoters, include, but are not limited to, crown ethers, such as benzo-15-crown-5.

Removal of the protecting groups, for example, by catalytic hydrogenation of the alkyl moiety, yields 2-ME2. Unfortunately, this synthetic route yields about 1–2% impurity of estradiol from the methoxylation step (a hydride quenches the reactive copper complex rather than a methoxide). The estradiol can be removed to undetectable levels by chromatography, such as described below, or significantly reduced by successive crystallization in chloroform.

Figure 13:
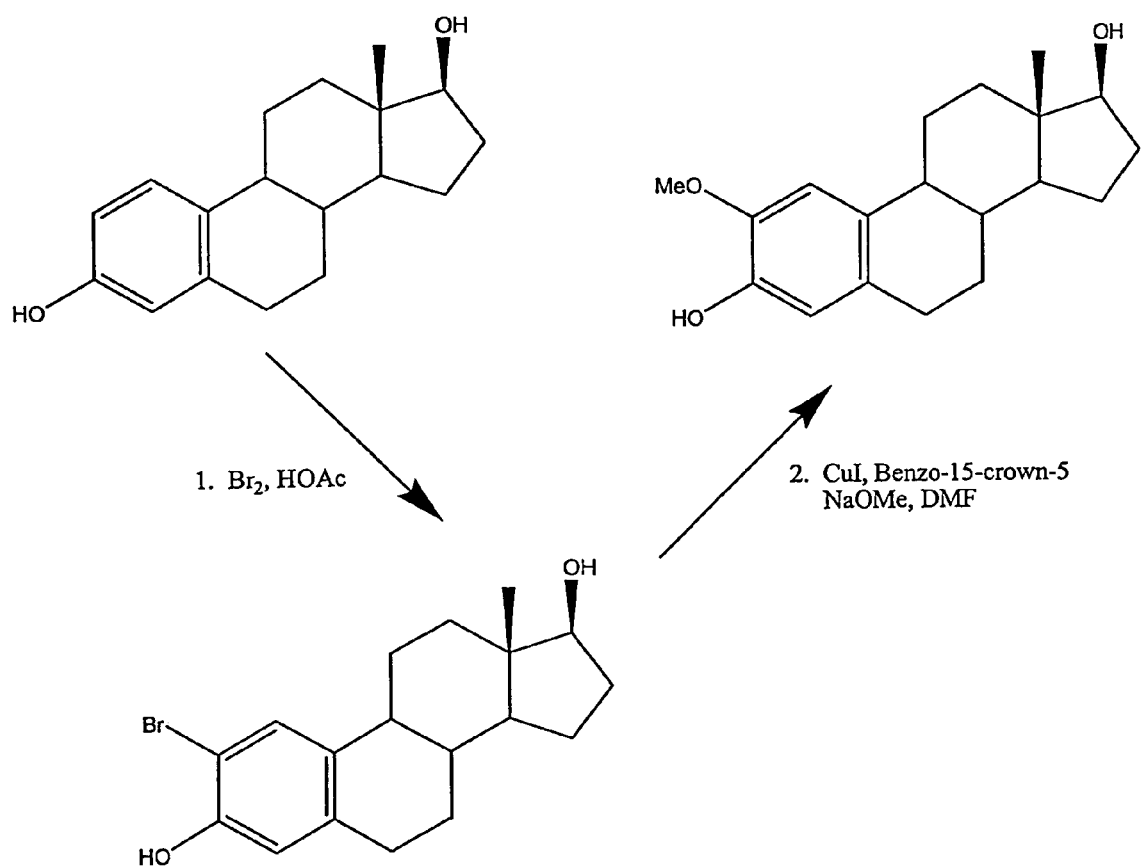
FIG. 13 depicts a synthetic reaction scheme for the production of the 2-methoxyestradiol of the present invention, using estradiol as a starting material and employing bromination at the 2-position of the A ring of unblocked estradiol and a crown ether.

Another synthetic method utilizing a brominated intermediate and employing estradiol as the starting material is illustrated by FIG. 13. In this synthetic reaction, the estradiol is ring brominated without first blocking the hydroxyl groups. The bromine is then replaced with a methoxide using a copper catalyst in a manner similar to that described above.

Figure 14:
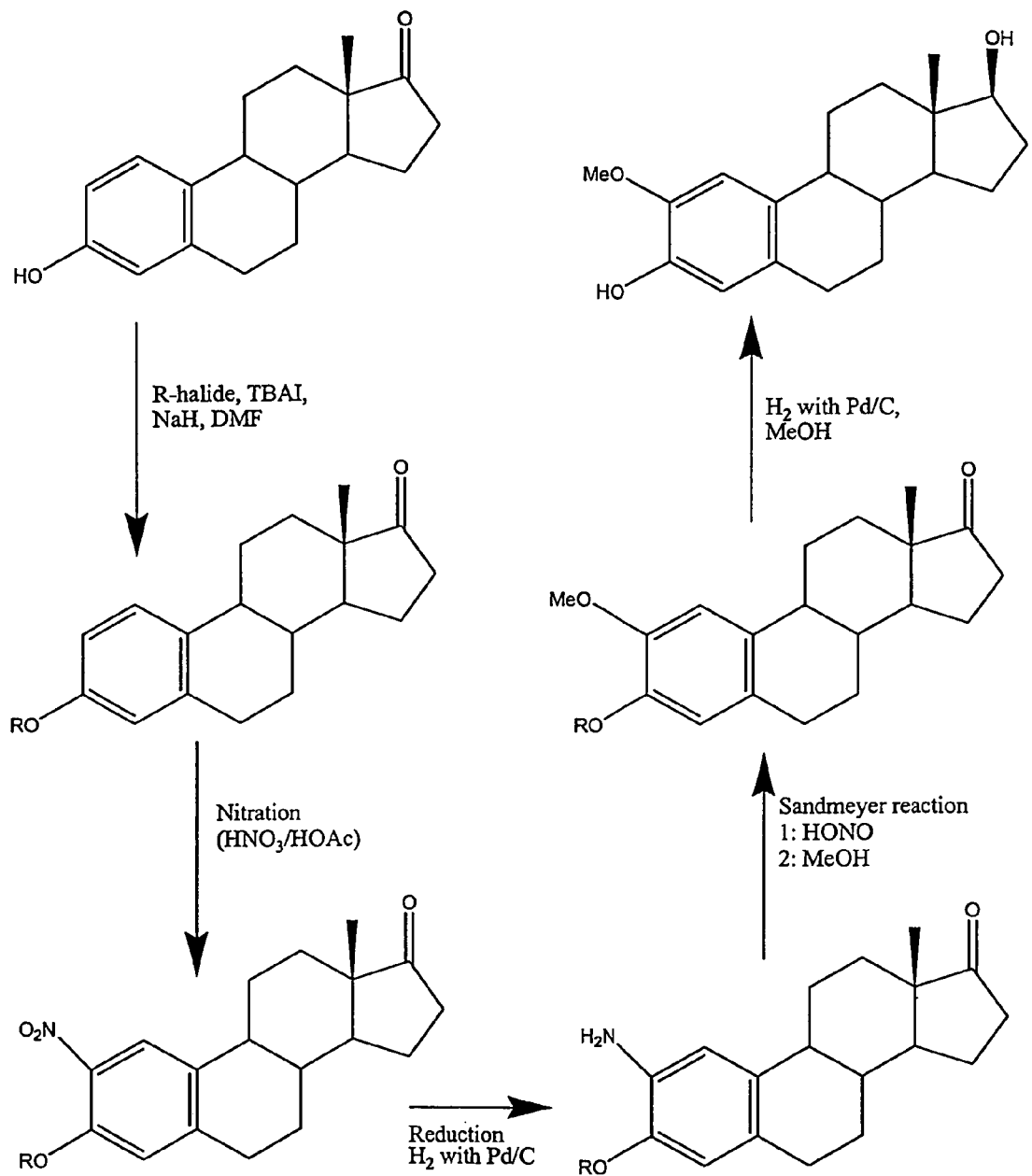
FIG. 14 depicts a synthetic reaction scheme for the production of the 2-methoxyestradiol of the present invention, using estradiol as a starting material and employing a blocking group on the 3- and 17-position hydroxyloxygen atoms of estradiol, nitration, and a Sandmeyer reaction.
Figure 15:
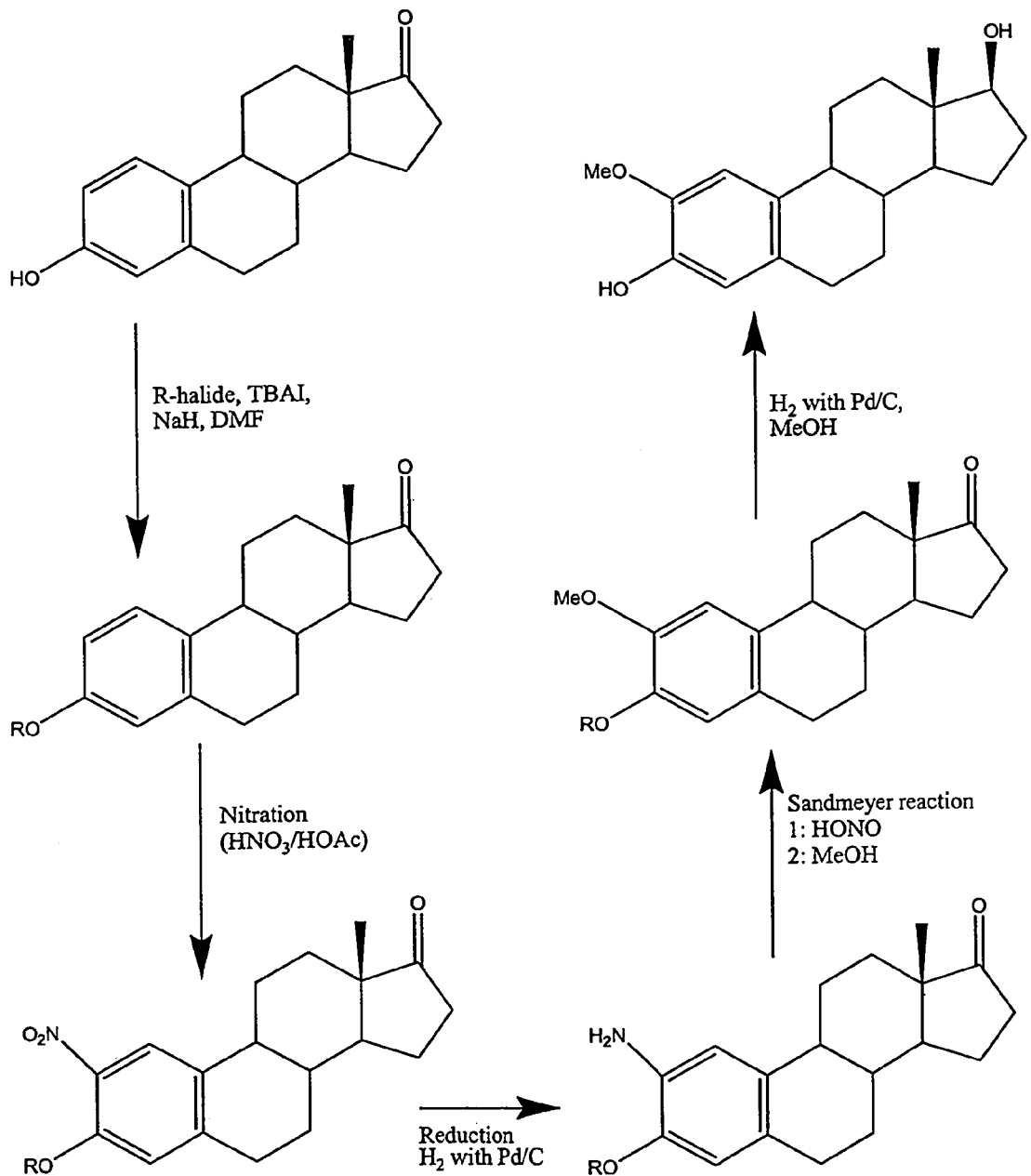
FIG. 15 depicts a synthetic reaction scheme for the production of the 2-methoxyestradiol of the present invention, using estrone as a starting material and employing a blocking group on the 3-position hydroxyloxygen atom, nitration, and a Sandmeyer reaction.

In another approach, estradiol or estrone can be used as a starting material in a reaction scheme that utilizes nitro/amine intermediates (see Cushman, M. et al., J. Med. Chem. 1995, 38, 2041). These synthetic approaches are illustrated in FIG. 14 (estradiol starting material) and FIG. 15 (estrone starting material). In these approaches, the free hydroxyl groups are protected. This protection can be accomplished, for example, using an alkyl halide, such as benzyl bromide, to form an alkyl ether. Appropriate conditions for hydroxyl protection include reaction of the starting material and alkyl halide in the presence of NaH and TBAI, optionally in the presence of a solvent, such as dimethyl formamide (DMF).

The protected starting material is then nitrated, for example, with nitric acid and acetic acid or with nitric acid and sulfuric acid, to form the corresponding 2-nitro product. The nitro group is then reduced. Selective reduction can be accomplished by catalytic hydrogenation, for example, hydrogenation in the presence of Pd/C to produce the corresponding 2-amine. The catalytic reduction is optimally carried out for a period of one hour. Using Sandmeyer conditions (nitrous acid and sodium methoxide), the 2-amino group can be converted to the 2-methoxy substituent. Catalytic hydrogenation removes the protecting groups to give 2-ME2 when the starting material is estradiol and 2-methoxyestrone when the starting material is estrone. Reduction of the 17-keto group of 2-methoxyestrone with sodium borohydride yields 2-ME2.

Yet another method employs estradiol as the starting material and utilizes brominated intermediates. In this synthetic reaction, the estradiol is ring brominated without first blocking the hydroxyl groups. Bromination is accomplished, for example, with bromine and acetic acid in a solvent, such as THF. This reaction results in bromination at different sites on the ring, including multi-brominated species. The 2-bromo-estradiol can then be isolated from the other brominated intermediates, for example, by chromotography or crystallization, followed by replacement of the bromine with a methoxide. The bromine can be replaced with a methoxide group, for example, using sodium methoxide and methanol in the presence of a copper catalyst, such as CuI, in a manner similar to that described above. Alternatively, the intermediates can be reacted to form the corresponding methoxides, followed by isolation of the 2-methoxyestradiol by the methods described above.

Methods of Purification

The present invention provides methods of purifying 2-ME2 to a purity of greater than 98.0%, more preferably greater than 99.0% and most preferably of 99.5% or higher. The 2-ME2 preparations preferably contain less than 0.03% estradiol, 0.02% or less 2-hydroxyestradiol, 0.02% or less 4-hydroxyestradiol, 0.02% or less 4-methoxyestradiol, and less than 0.02% estrone. Most preferably, the 2-ME2 preparations contain 0.01% or less estradiol, 0.02% or less 2-hydroxyestradiol, 0.01% or less 4-hydroxyestradiol, 0.01% or less 4-methoxyestradiol, and 0.01% or less estrone.

The purification methods of the present invention involve liquid chromatography on an adsorption/partition medium such as silica, using a solvent system comprising a polar and a non-polar solvent. The purification methods described herein can also be used, with minor modifications, to purify compounds similar to 2-ME2, such as, for example, 4-methoxyestradiol, 4-hydroxyestradiol, 2-hydroxyestradiol, estradiol, estrone, 2-methoxyestrone, and 4-methoxyestrone.

The Sample

The sample to be purified can be synthesized, or obtained from a biological source. The sample may be a commercially available 2-ME2 preparation, such as those sold by Sigma-Aldrich Chemicals of St. Louis, Mo., Research Plus, Inc. of Bayonne, N.J., or Calbiochem of San Diego, Calif. The sample is preferably at least about 50% pure, more preferably about 75% pure, even more preferably about 90% pure, and most preferably about 98% pure. The sample can be subjected to other purification steps prior to the methods described herein, such as selective crystallization.

The sample is preferably dissolved into or solvent-exchanged into a loading solvent, as further described below. The sample is preferably at a concentration in the range of about 0.01 to 2 g/ml, preferably about 0.01 to 1 g/ml, more preferably about 0.05 to 0.2 g/ml.

Chromatographic Media

Silica is preferably used as the chromatographic medium. Silica gel of about 70–400 mesh is preferred, most preferably about 70–230 mesh, such as supplied by Merck and other vendors. The medium can be used loose, in batch chromatography, or packed into a column. Pre-packed columns, such as those sold by Biotage of Charlottesville, Va., can also be used. The medium should be equilibrated in an appropriate solvent before application of the sample to the medium, as further discussed below.

Column Dimensions

The chromatographic methods described herein can be achieved using batch or column chromatography. In batch chromatography, the sample and the chromatographic medium are combined in a container for a period of time sufficient to allow the 2-ME2 to be retained by the medium. The medium is then preferably washed with wash solvent. Elution solvents are then applied to the medium. After the loading, wash, and elution steps, the solvent is removed from the medium, such as by filtration.

For column chromatography, a column having appropriate dimensions is packed with the chromatography medium. The column, after equilibration with appropriate solvent, is loaded with sample by applying the sample to the top, or entrance, of the column. The ratio of the sample volume to column diameter should preferably be between about 0.2 to 3 ml/cm, and more preferably between about 0.5 and 1.5 ml/cm for best results.

Solvents

A solvent system including a polar solvent, such as methanol (MeOH), and a non-polar solvent, such as chloroform ($CHCl_3$), is used. Other polar solvents that can be used include, but are not limited to, tetrahydrofuran (THF), ethyl acetate, isopropanol, ethanol, propanol, and combinations thereof. Other non-polar solvents that can be used include, but are not limited to, hexane, dichloromethane, cyclohexane, pentane, and combinations thereof. More specifically, solvent systems that can be used include THF/hexane, ethyl acetate/hexane, isopropanol/hexane, ethanol/$CHCl_3$, propanol/$CHCl_3$, isopropanol/$CHCl_3$, and combinations thereof.

The sample is soluble in the polar solvent. Some amount of the polar solvent, generally about 10%, is needed to render the sample soluble in the loading solvent. The loading solvent thus will include up to about 10% polar solvent and about 90% non-polar solvent.

After the sample is loaded onto the medium, the medium may be washed with a wash solvent that will wash contaminants off the medium but will not elute the 2-ME2. The wash solvent comprises mostly non-polar solvent, with enough polar solvent to prevent the 2-ME2 from precipitating but not enough polar solvent to elute the 2-ME2.

The sample is eluted with elution solvent that contains enough polar solvent to elute the 2-ME2 from the medium. The elution solvent may be applied as a step gradient or as a linear gradient, as described below.

Column Conditions

The wash and elution solvents can be applied to the column in a step gradient or in a linear gradient. In a preferred embodiment, the solvents are applied using a step gradient of increasing concentration of polar solvent.

The column can be operated using the force of gravity or can be operated with a pump that forces liquids through the column. The rate at which the column is operated will depend upon the volume and dimensions of the column and the silica gel particle size. In general, the column can be operated at a rate from about 0.5 to 5 ml/min.

The eluant can be monitored visually or, monitored with a spectrophotometer at a wavelength of about 288 nm, which is the absorbance maximum of 2-ME2, and collected as the 2-ME2 elutes from the column.

The column can optionally be operated under pressure and can optionally be heated. Preparative high performance liquid chromatography (HPLC), either normal phase or reversed phase, or fast performance liquid chromatography (FPLC) techniques can be used. Commercial preparative chromatography apparatus, such as that sold by Biotage of Charlottesville, Va., can also be used. Other known methods of improving column efficiency and/or speed can also be employed.

Sample Collection and Treatment

The eluant can be collected as fractions which are then assayed for 2-ME2 content and purity. These fractions can then be combined to achieve the desired purity of 2-ME2. The fractions can be assayed for purity using reverse phase HPLC with a C-18 column (Waters) and an isocratic solvent system of 30:69:1 acetonitrile:water:acetic acid. Other systems can be used for sample analysis, such those that use solvent gradients instead of the isocratic solvent system; those that use trifluoroacetic acid or formic acid rather than acetic acid; and those that use methanol rather than acetonitrile.

Alternatively, or in combination, the eluant can be monitored in real time and sample collection begun when 2-ME2 of desired purity elutes from the column.

The solvent is removed from the pooled fractions by use of a vacuum and/or other solvent removal methods. Lyophilization and other evaporative methods can be used.

PREFERRED EMBODIMENT

In a preferred embodiment the medium is silica, which is packed into a column. The sample is dissolved in a mixture of $CHCl_3$ and MeOH, with enough MeOH to solubilize the 2-ME2, generally about 90:10 $CHCl_3$:MeOH. The elution conditions are a step gradient from 99:1 $CHCl_3$:MeOH to 98:2 $CHCl_3$:MeOH.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Commercially available samples of 2-ME2 were assayed by analytical HPLC to determine their overall purity and the amounts of certain contaminants, namely estradiol, 4-hydroxyestradiol, 4-methoxyestradiol, 2-hydroxyestradiol, estrone, and 2-methoxyestrone.

These analytical HPLC chromatograms were generated using reverse phase HPLC with a C-18 column (Waters) and a solvent gradient (20 to 50% acetonitrile over 30 minutes, 50 to 80% acetonitrile over 5 minutes, 1% acetic acid, remainder water). The eluant was monitored at a wavelength of 288 nm. In this system 2-ME2 elutes at about 21.5 minutes, estradiol elutes at about 20.0 minutes, estrone elutes at about 23.2 minutes, 4-hydroxyestradiol elutes at about 15.0 minutes, 4-methoxyestradiol elutes at about 20.4 minutes, 2-hydroxyestradiol elutes at about 15.4 minutes, and 2-methoxyestrone elutes at about 24.4 minutes.

Figure 1:
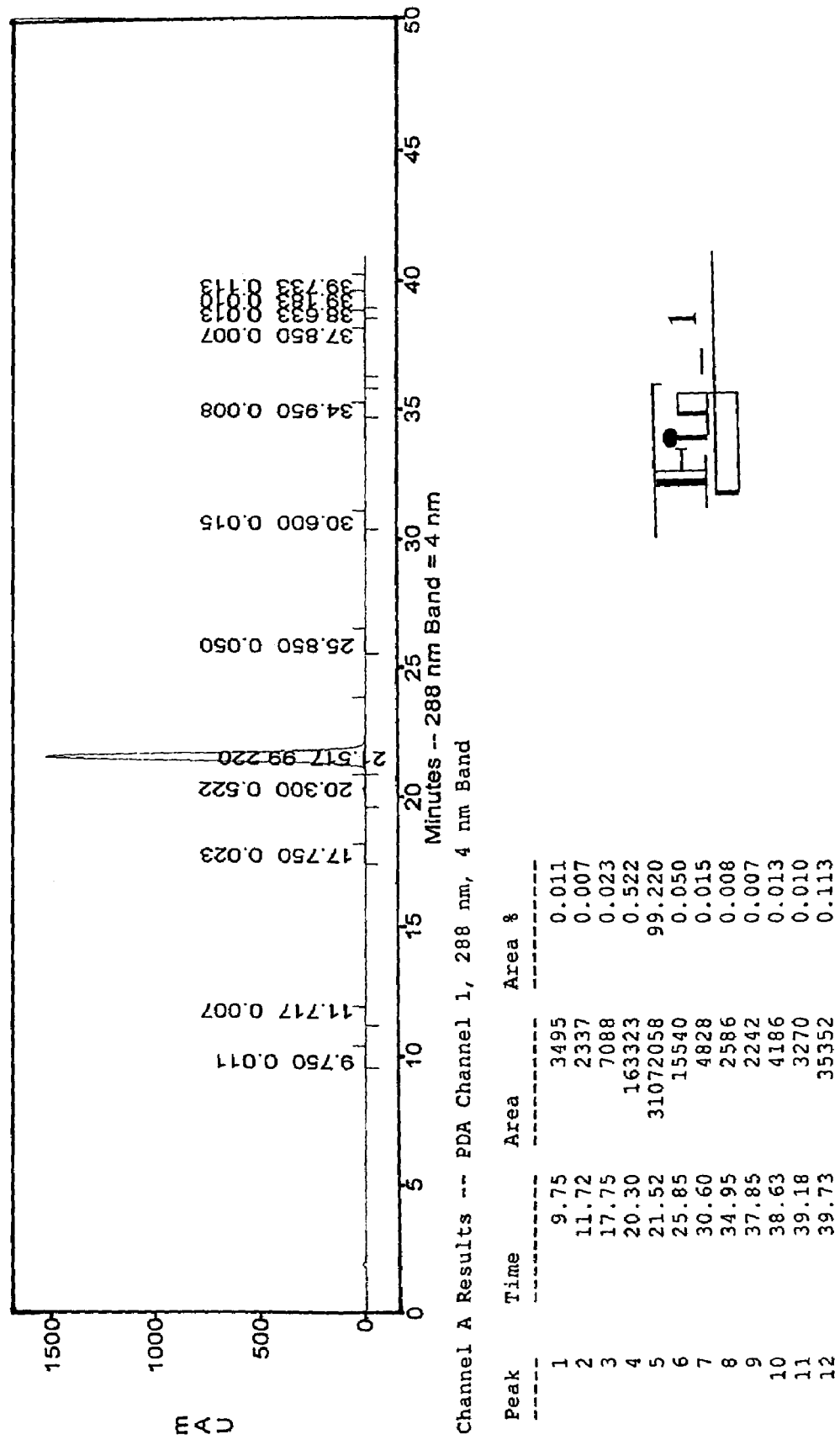
FIG. 1 is a chromatogram from the reversed phase HPLC analysis of 2-methoxyestradiol available from Sigma Chemical Company (45H4033). This graph shows that the Sigma product contains about 0.034% estradiol.
Figure 2:
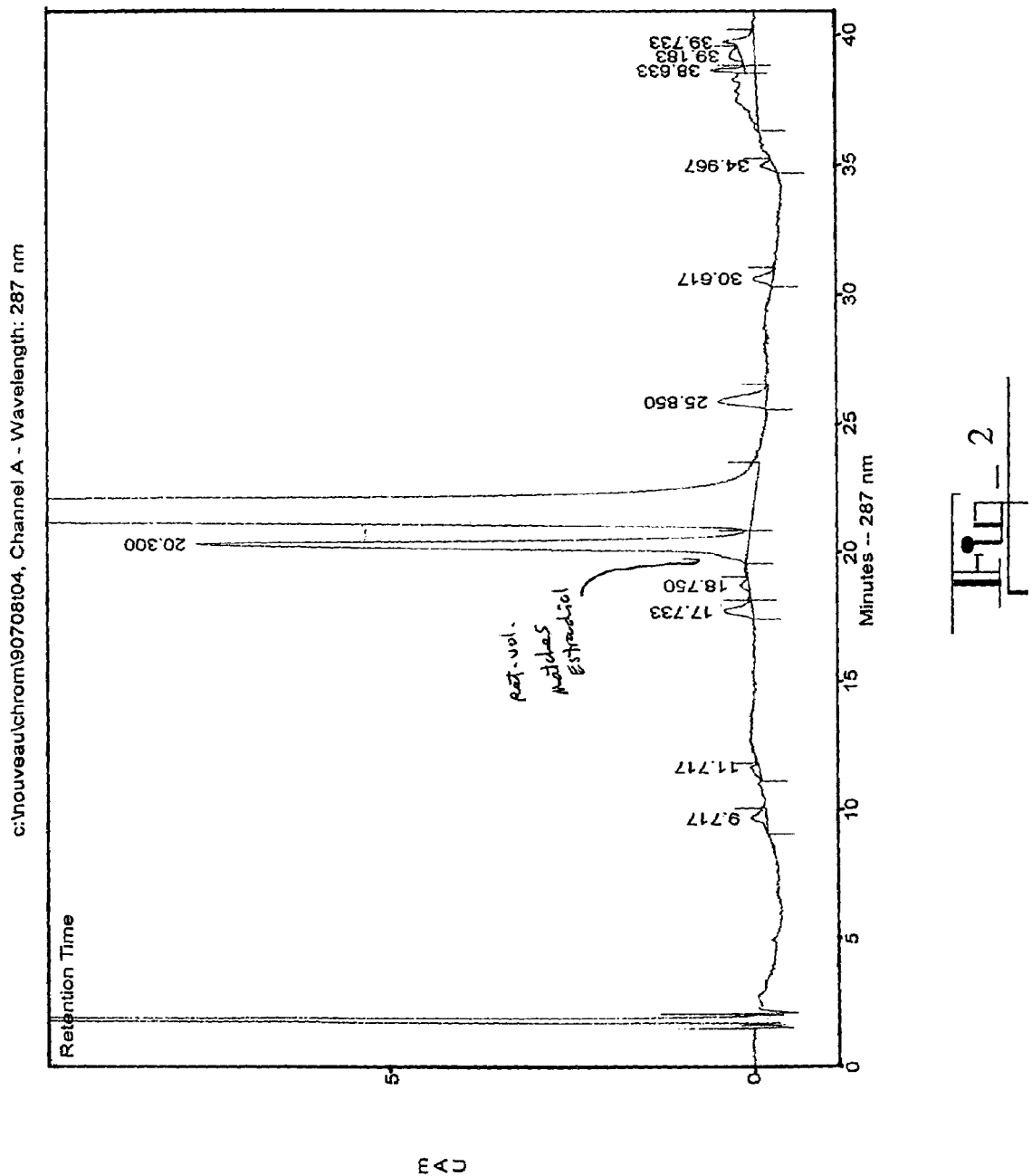
FIG. 2 is an expanded view of the chromatogram in FIG. 1 indicating the estradiol impurity.

The chromatogram of a sample from Sigma-Aldrich Chemicals of St. Louis, Mo. is shown in FIG. 1. The sample has an overall purity of 99.2% but has contaminating estradiol of about 0.034%, an unacceptable amount. FIG. 2 is an expanded view of the chromatogram of FIG. 1.

Figure 3:
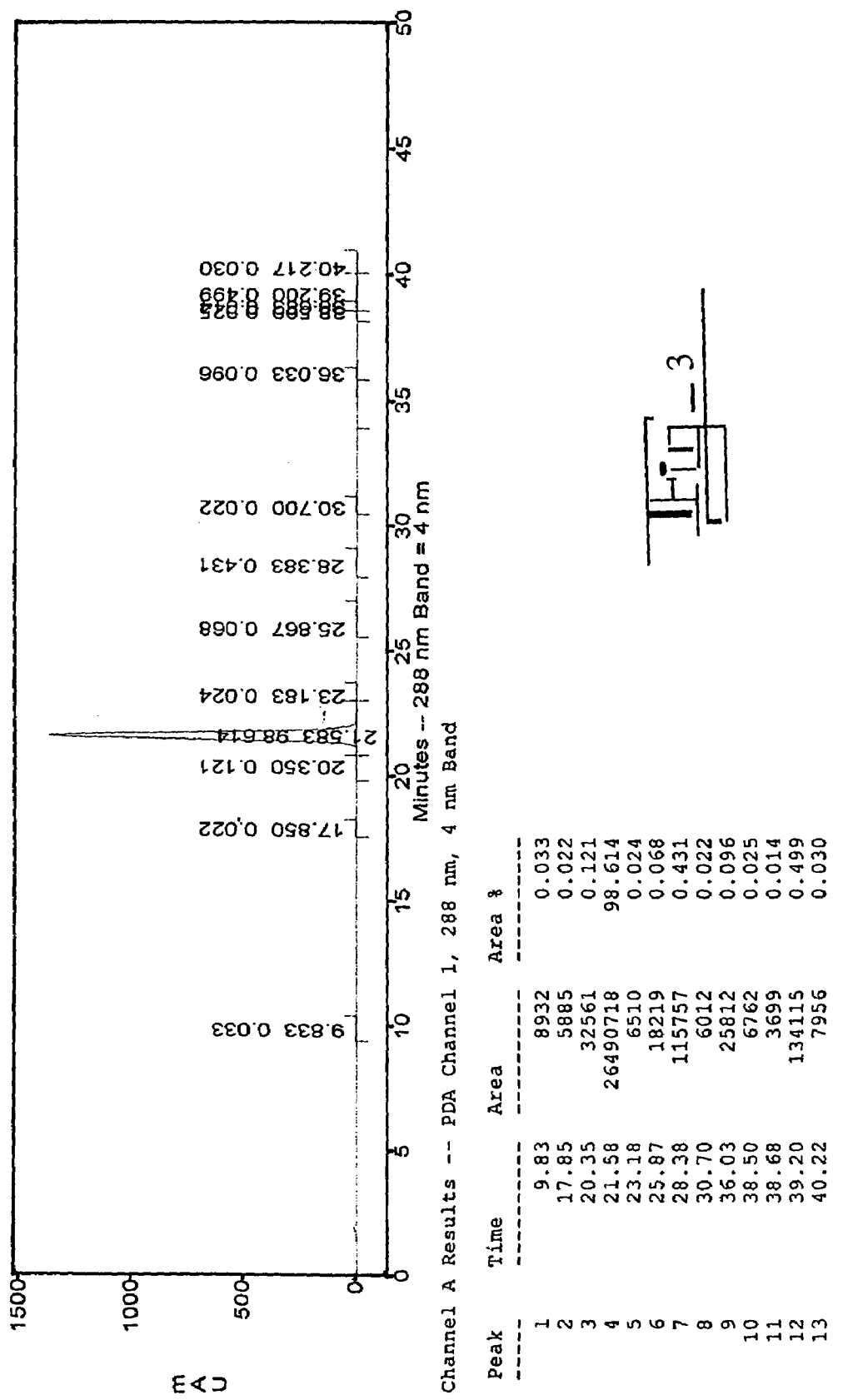
FIG. 3 is a chromatogram from the reversed phase HPLC analysis of 2-methoxyestradiol available from Research Plus (10699). This graph shows that the Research Plus product contains about 0.024% estrone and about 0.93% other undesirable estrogens.
Figure 4:
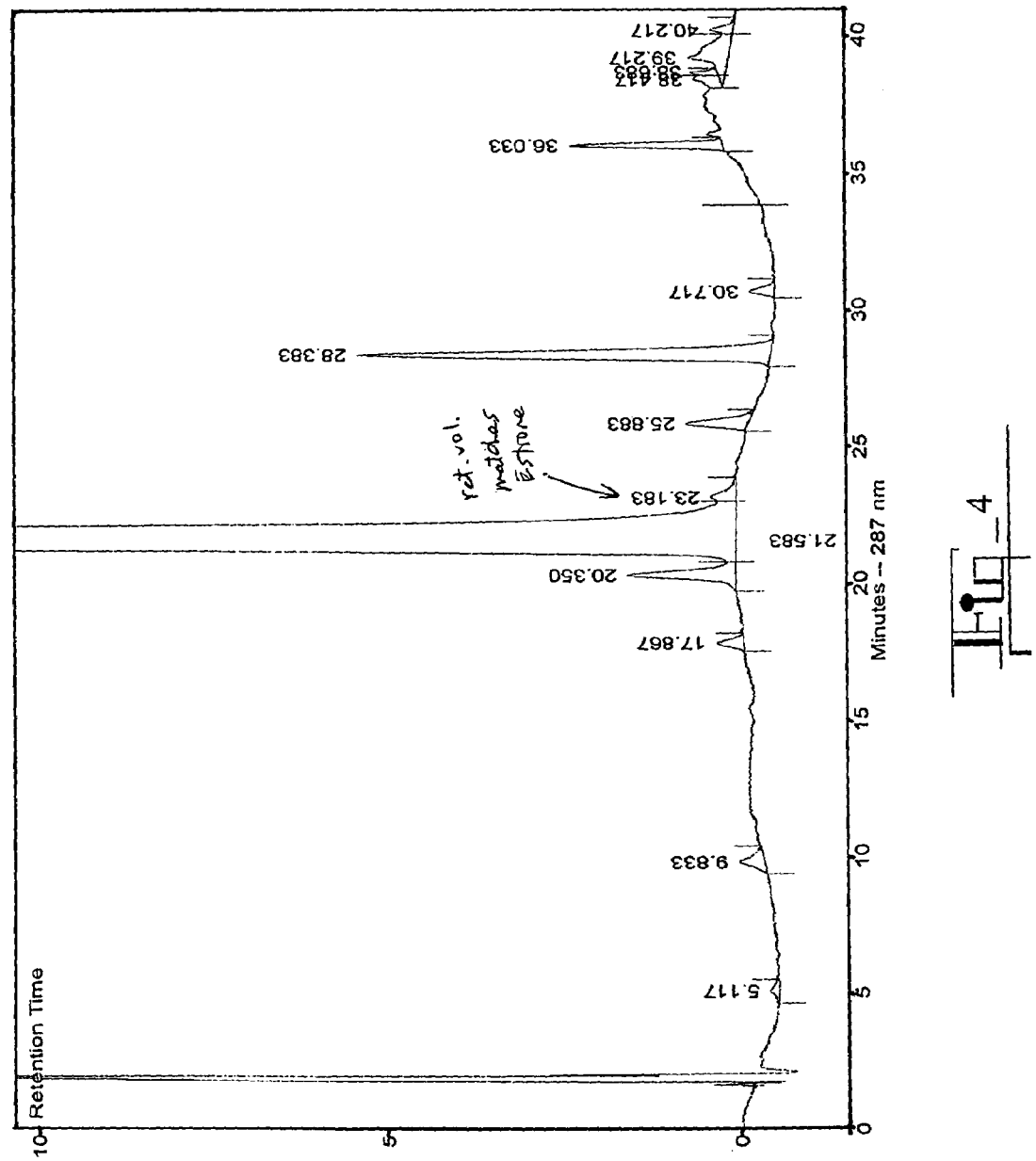
FIG. 4 is an expanded view of the chromatogram in FIG. 3 indicating the estrone impurity.

FIG. 3 is a chromatogram of a sample obtained from Research Plus, Inc. of Bayonne, N.J. that shows that the 2-ME2 has a purity of 98.6%. The automatic peak calculator and the expanded view shown in FIG. 4 show that the preparation contains 0.024% estrone, an unacceptable amount of this contaminant. Other samples tested showed 2-ME2 purity less than 98%, including a second batch obtained from Research Plus (97.2% 2-ME2) and a sample from CalBiochem of San Diego, Calif. (91.8% 2-ME2).

Table 1, below, illustrates the purity and contaminants of these commercially available samples of 2-ME2 and the purified 2-ME2 of the present invention.

TABLE 1

|  | Sigma | Research Plus, Lot #1 | Research Plus, Lot #2 | Calbiochem | PharmEco | purified |
|---|---|---|---|---|---|---|
| 2-ME2 | 99.18 | 98.61 | 97.17 | 91.80 | 97.80 | 99.98 |
| estradiol | 0.03 | n.d. | n.d. | 1.78 | 2.2 | less than 0.01% |
| estrone | n.d. | 0.02 | 0.43 | 0.011 |  | n.d. |
| 4-hydroxyestradiol | n.d. | n.d. | n.d. | n.d. |  | n.d. |
| 4-methoxyestradiol | 0.49 | 0.121 | 0.18 | 1.99 |  | n.d. |
| 2-hydroxyestradiol | n.d. | n.d. | n.d. | 0.06 |  | n.d. |
| 2-methoxyestrone | n.d. | n.d. | n.d. | 0.20 |  | n.d. |

*n.d. means none was detected.

EXAMPLE 2

A 55 cm diameter (60 cm height) glass column was packed with 600 g silica gel (70–230 mesh from Merck) in 90:10 $CHCl_3$:MeOH. The column was washed with one liter of $CHCl_3$ to remove the MeOH from the column.

Figure 5:
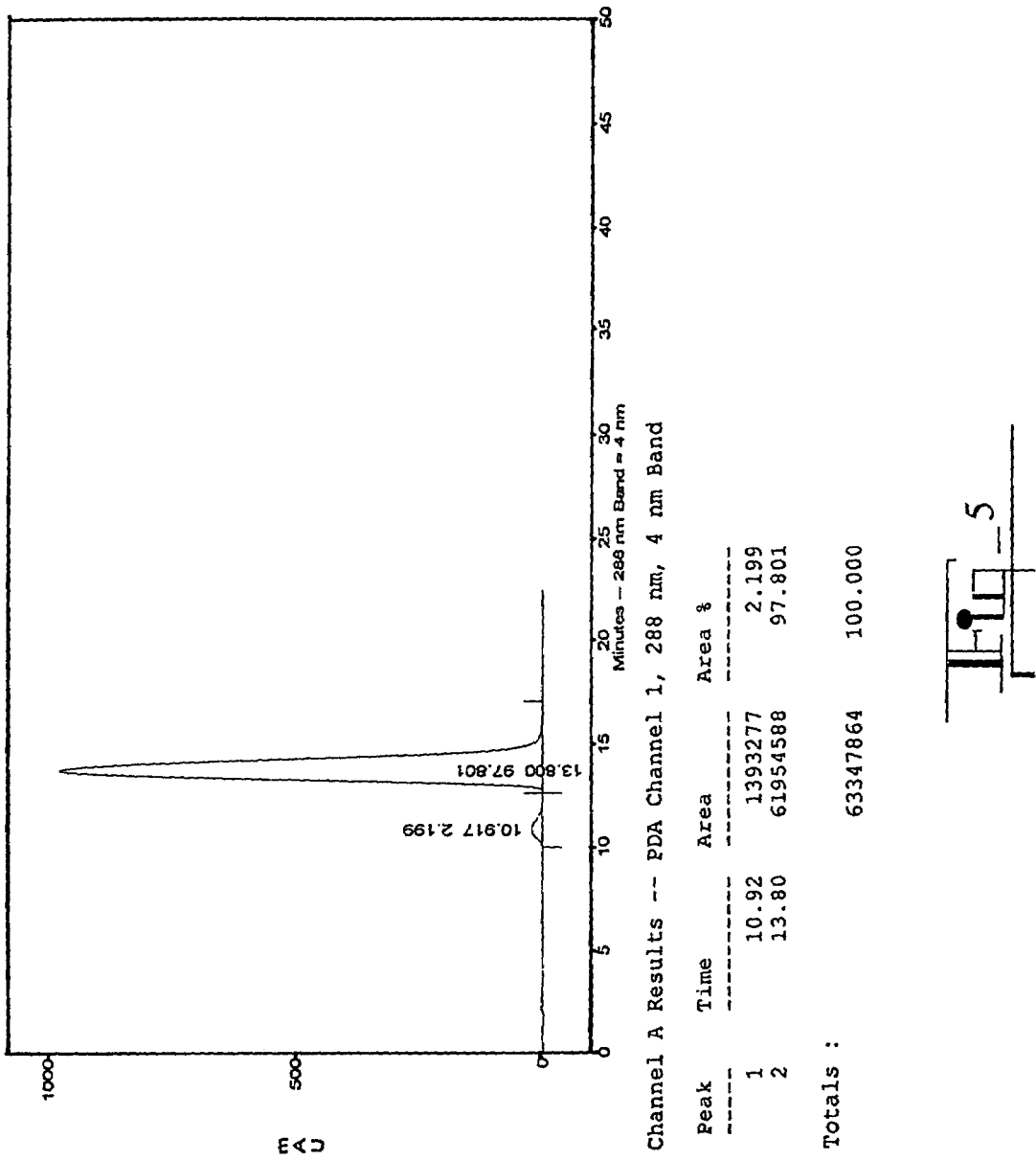
FIG. 5 is a chromatogram from the reversed phase HPLC analysis of the unpurified 2-methoxyestradiol employed as the starting material in Example 2 of the present invention.

The sample was 3.5 g 2-ME2 in 60 ml 90:10 $CHCl_3$:MeOH. The 2-ME2 was obtained from PharmEco Laboratories, Inc. of Lexington, Mass., and was 97.8% pure as determined by analytical HPLC (FIG. 5). The peak eluting at 10.917 is estradiol (2.2%).

Analytical HPLC of the starting material, the column fractions, and the pooled product was performed using reverse phase HPLC with a C-18 column (Waters) and an isocratic gradient of 30:69:1 acetonitrile:water:acetic acid, which provides good separation of 2-ME2 and estradiol. The eluant was monitored at a wavelength of 288 nm.

The sample was applied to the top of the column and allowed to enter the bed volume. The column was eluted with one liter of 99:1 $CHCl_3$:MeOH and then 1.5 L of 98:2 $CHCl_3$:MeOH. Fractions of 50 ml each were collected and 15 fractions containing 2-ME2 were assayed for 2-ME2 purity using the analytical isocratic HPLC system described above. Nine to ten fractions that showed no amount of estradiol were pooled together and solvent was evaporated. After drying under vacuum for 4 hours, 3.2 g of yellow/white crystals were collected, for a 91% yield.

Figure 7:
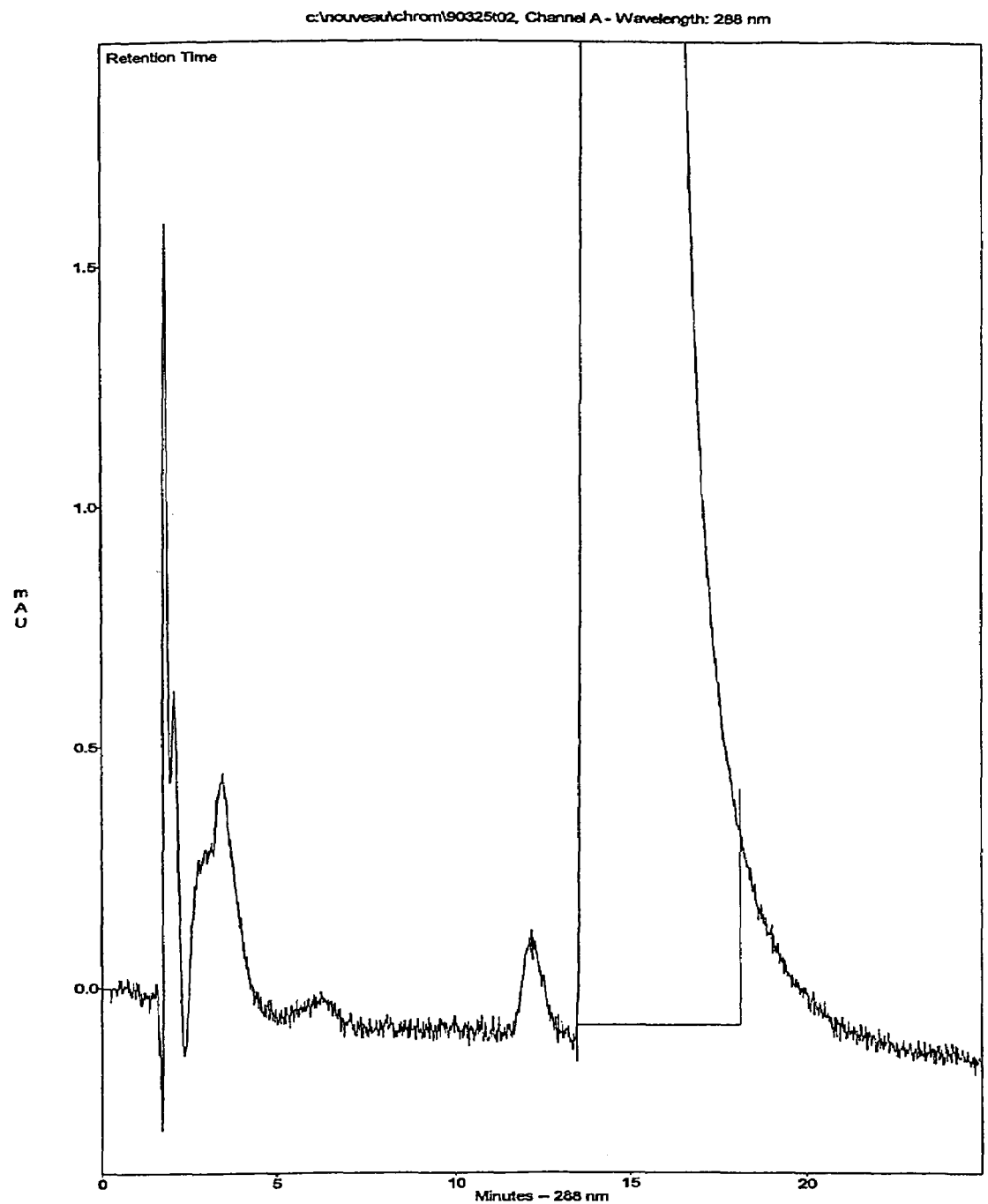
FIG. 7 is an expanded view of the chromatogram in FIG. 6.
Figure 8:
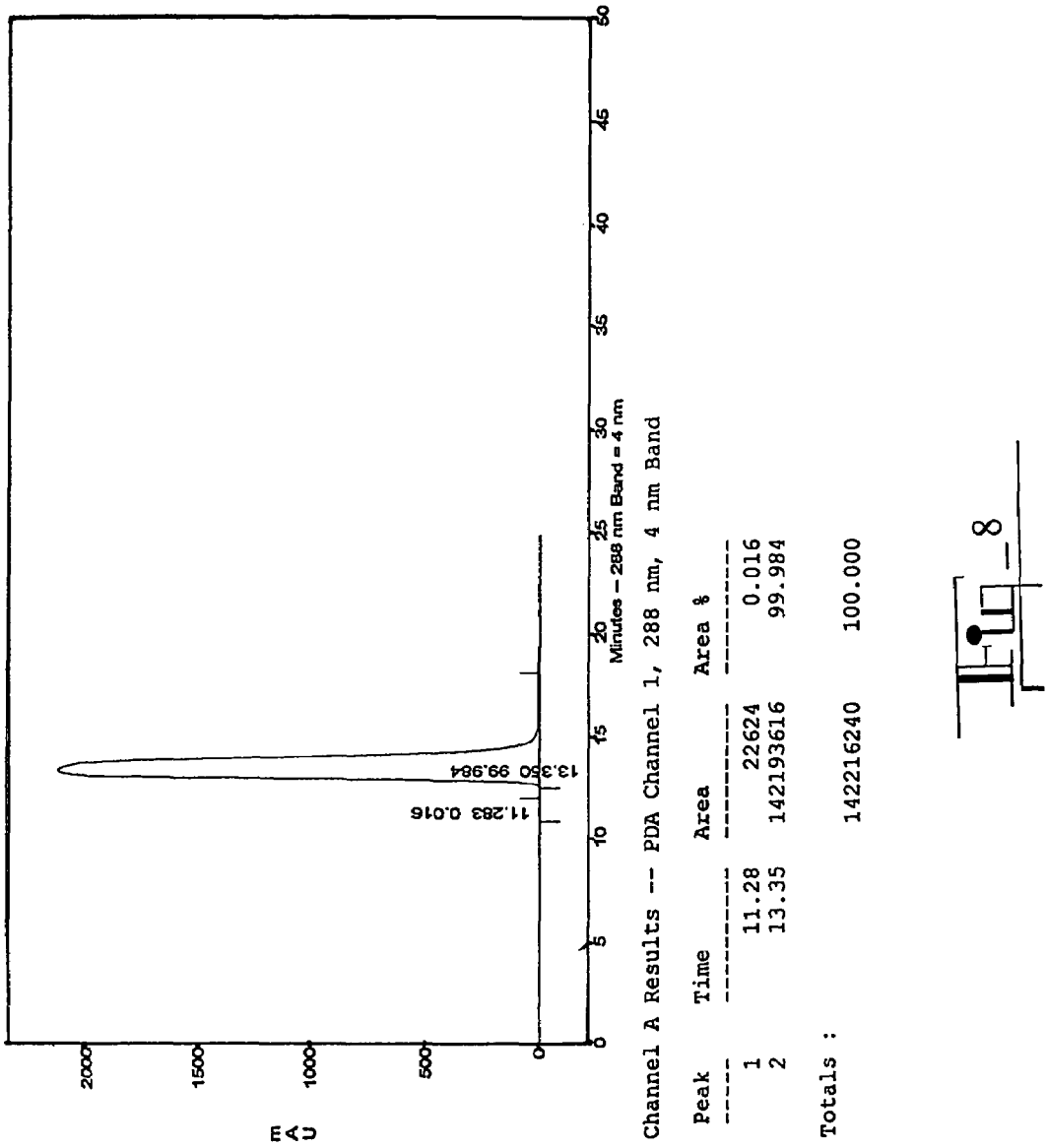
FIG. 8 is a chromatogram of the 2-ME2 of the present invention produced in Example 2. The HPLC was run with an overloaded amount of sample, 270 µg (50 µl at 5.4 µl/ml).
Figure 9:
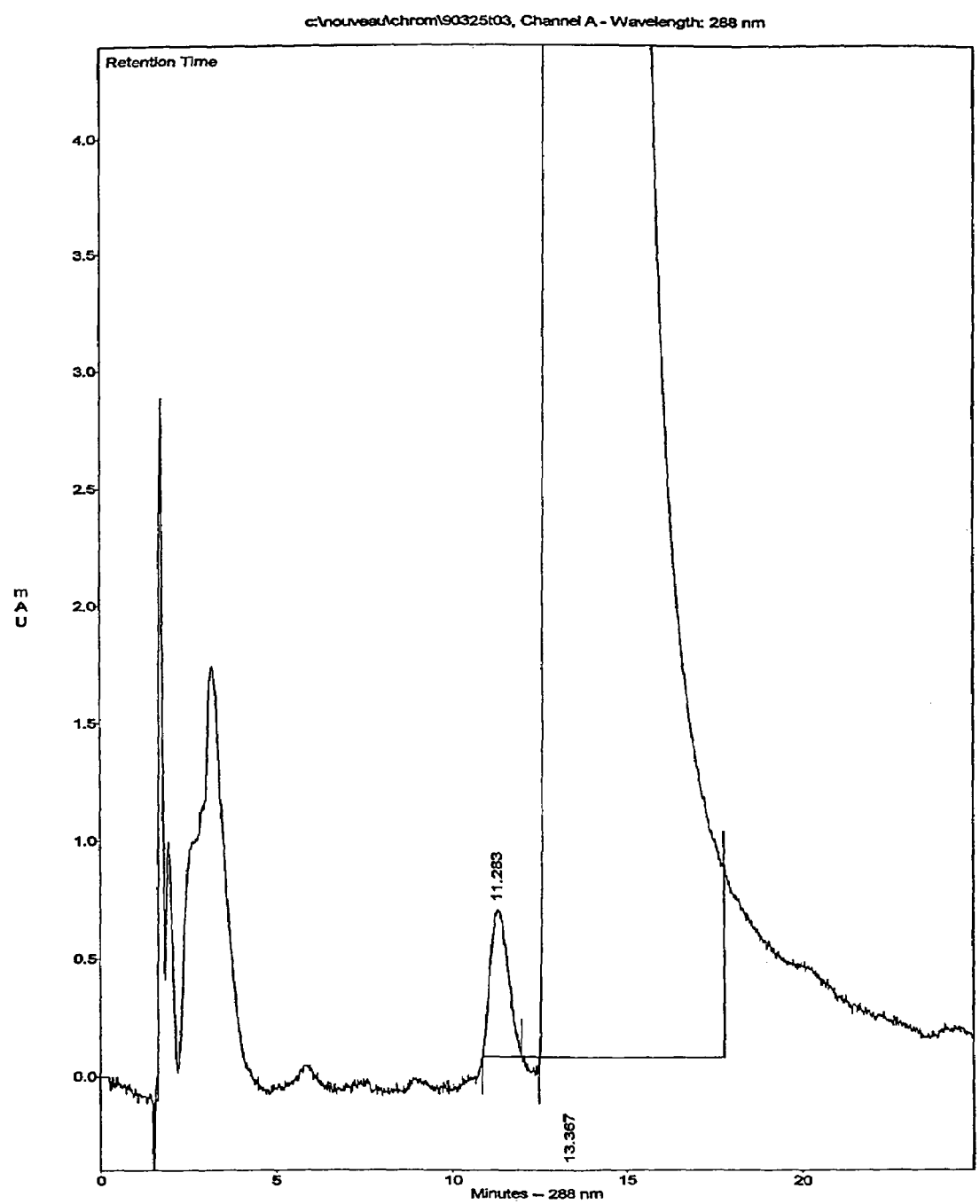
FIG. 9 is an expanded view of the chromatogram in FIG. 8.

Purity of the pooled fractions was determined by analytical HPLC to be 99.984%, using the isocratic technique described above. The HPLC chromatograms are shown in FIGS. 6 through 9. FIG. 6 was generated with a non-overloaded amount of sample, 75.6 μg (14 μl at 5.4 μl/ml). FIG. 7 is an expanded view of the chromatogram of FIG. 6. The automatic peak finder calculated the 2-ME2 to be 100.0%, although a small, unknown impurity peak is seen in the expanded view, eluted prior to the 2-ME2. FIG. 8 was generated with an overloaded amount of sample, 270 μg (50 μl at 5.4 μl/ml). FIG. 9 is an expanded view of the chromatogram of FIG. 8. The automatic peak finder calculated the 2-ME2 to be 99.984% pure, with a small, unknown, impurity that eluted prior to the 2-ME2, and after estradiol, that was calculated to be 0.016%. The expanded view shown in FIG. 9 shows this impurity peak more clearly and shows that the 2-ME2 peak is very clean.

Figure 10:
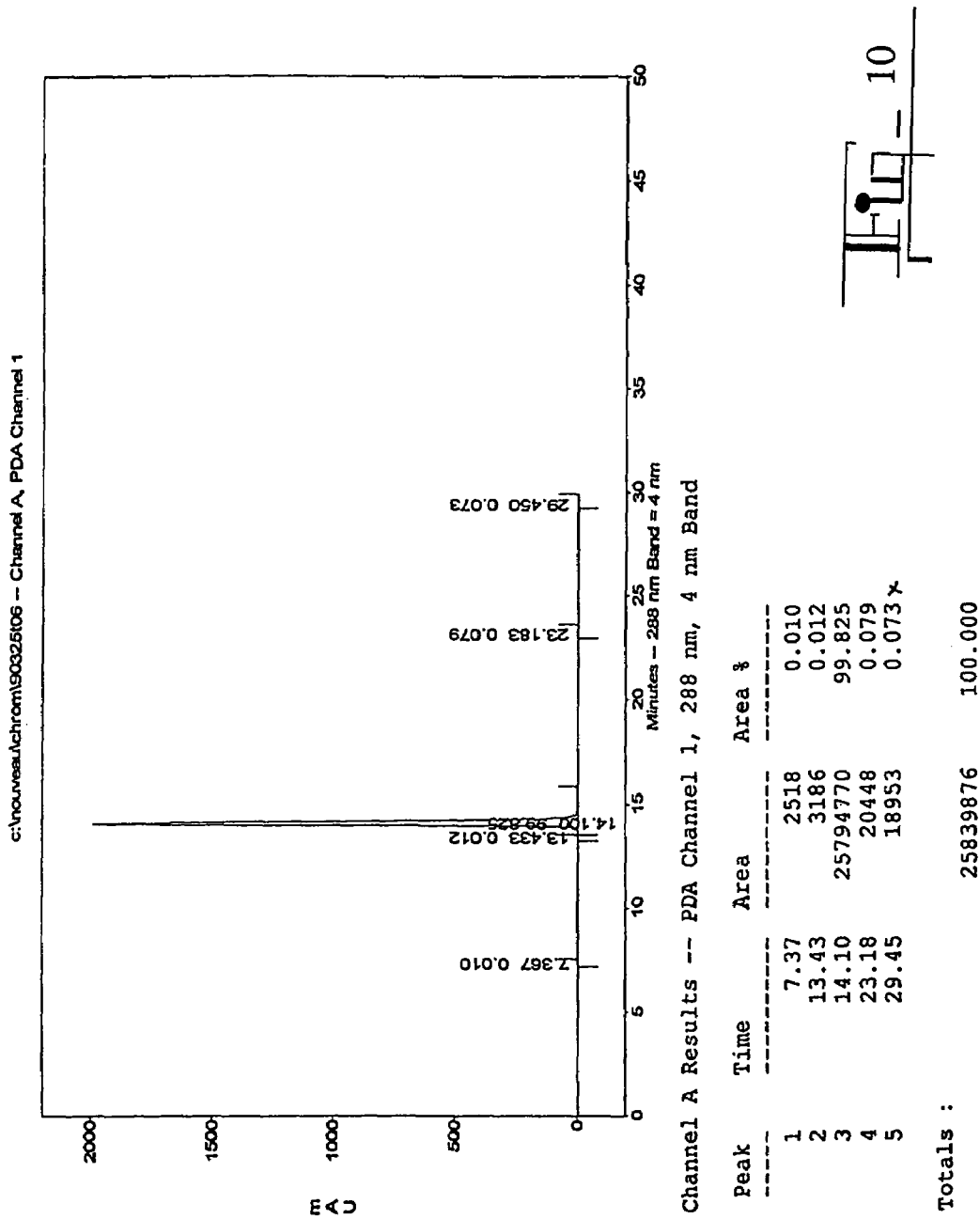
FIG. 10 is a chromatogram of the pooled fractions from Example 2, assayed using a gradient (20 to 70% acetonitrile over 25 minutes, 1% acetic acid, and remainder water). 43.2 µg (8 µl of the 5.4 µl/ml sample) was injected.
Figure 11:
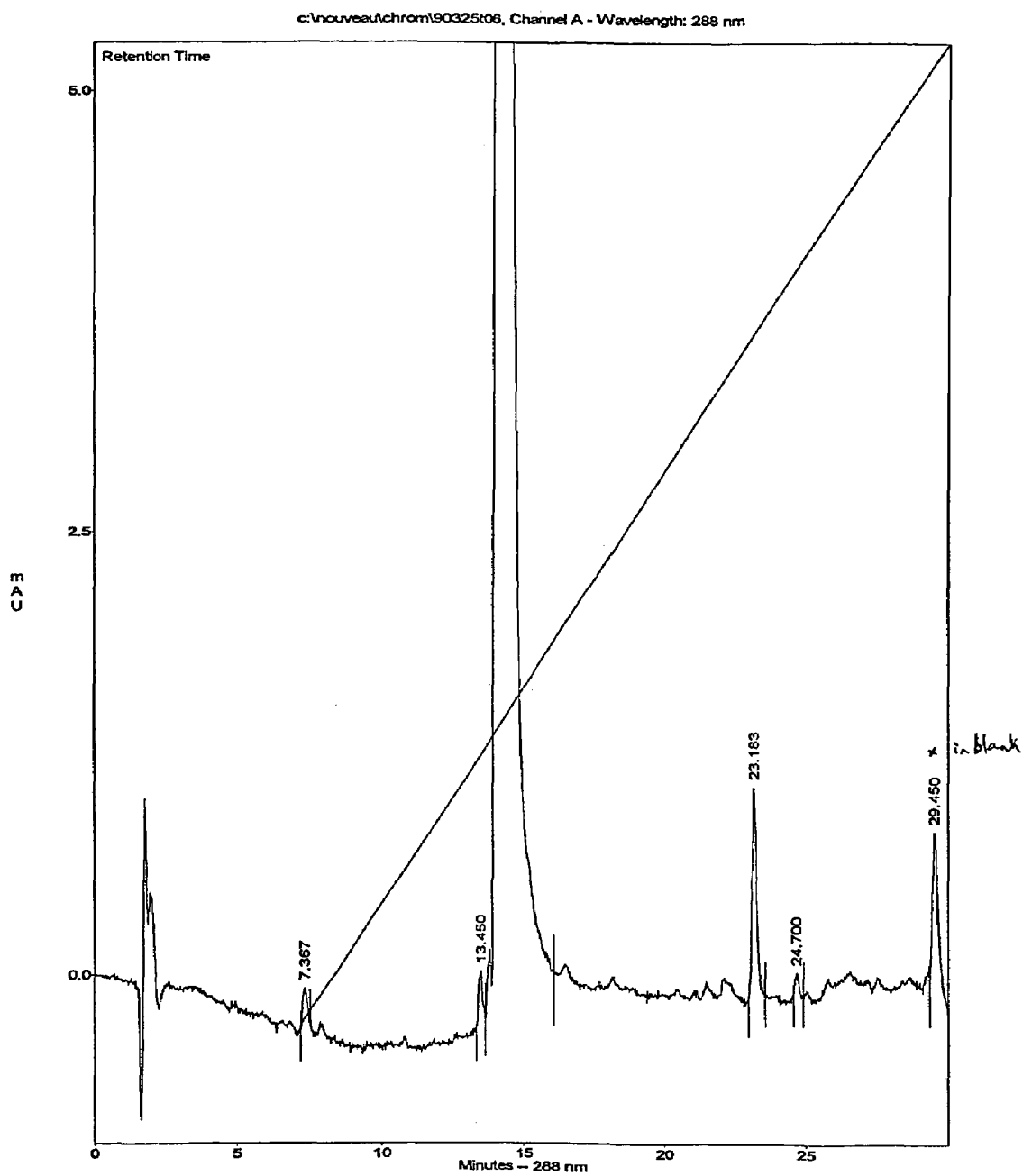
FIG. 11 is an expanded view of the chromatogram in FIG. 10.

The pool was also assayed using a gradient (20 to 70% acetonitrile over 25 minutes, 1% acetic acid, and remainder water). 43.2 μl (8 μl of the 5.4 μl/ml sample) was injected. The chromatogram is shown in FIG. 10. The automatic peak finder calculated the 2-ME2 to have a purity of 99.825%. However, when an artifact peak, present in a blank run, at 29.45 minutes is removed from consideration, the calculated purity is 99.9%. FIG. 11 is an expanded view of this chromatogram. The unknown impurity at 13.43 minutes was calculated to be 0.012%. If estradiol were present, it would elute between the unknown purity and the 2-ME2 peak. If estradiol is present, therefore, it can be present at no more than ⅓ to ¼ of the amount of the unknown peak. Accordingly, the estradiol amount was estimated to be no more than 0.004%. The preparation contained 0.02% or less 2-hydroxy-estradiol, 0.01% or less 4-hydroxy-estradiol, 0.01% or less 4-methoxy-estradiol, and 0.01% or less estrone, as demonstrated by the lack of any measurable peaks at the expected retention times.

The purified sample was also subjected to elemental analysis and the results are shown in Table 2.

TABLE 2

| Element | Elemental Analysis | |
|---|---|---|
| | Theoretical | Found |
| Carbon | 75.46 | 75.21 |
| Hydrogen | 8.67 | 8.65 |
| Oxygen | 15.87 | 16.13 (obtained by difference) |
| Chlorine | 0.00 | 0.0 |

The above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patents, patent applications and publications, are incorporated herein by reference.

What is claimed is:

1. A pharmaceutical composition being substantially free of steroid contaminants having estrogenic or carcinogenic effects comprising 2-methoxyestradiol having a purity greater than 99.5% as determined by HPLC.

2. The composition of claim 1, containing less than 0.03% estradiol and less than 0.02% estrone.

3. The composition of claim 2, containing less than 0.01% estradiol and less than 0.01% estrone.

4. The composition of claim 2, further containing less than 0.02% 2-hydroxyestradiol.

5. The composition of claim 2, further containing less than 0.02% 4-hydroxyestradiol.

6. The composition of claim 2, further containing less than 0.02% 4-methoxyestradiol.

7. The composition of claim 1, containing 0.01% or less estradiol, 0.02% or less 2-hydroxyestradiol, 0.01% or less 4-hydroxyestradiol, 0.01% or less 4-methoxyestradiol and 0.01% or less estrone.

8. A pharmaceutical composition being substantially free of steroid contaminants having estrogenic or carcinogenic effects comprising 2-methoxyestradiol having a purity greater than 98.0% and containing less than 0.03% estradiol and less than 0.02% estrone.

9. The composition of claim 8, containing less than 0.01% estradiol and less than 0.01% estrone.

10. The composition of claim 8, containing 0.01% or less estradiol, 0.02% or less 2-hydroxyestradiol, 0.01% or less 4-hydroxyestradiol, 0.01% or less 4-methoxyestradiol and 0.01% or less estrone.

11. The composition of claim 8, wherein the 2-methoxyestradiol has a purity greater than 99.0%.

12. The composition of claim 11, containing less than 0.01% estradiol and less than 0.01% estrone.

13. The composition of claim 11, containing 0.01% or less estradiol, 0.02% or less 2-hydroxyestradiol, 0.01% or less 4-hydroxyestradiol, 0.01% or less 4-methoxyestradiol and 0.01% or less estrone.

14. A method for purifying 2-methoxyestradiol to a produce a 2-methoxyestradiol substantially free of steroid contaminants having estrogenic or carcinogenic effects and having a purity greater than 98% and containing less than 0.03% estradiol and less than 0.02% estrone comprising:
adding a solution comprising 2-methoxyestradiol to a chromatography medium; and
eluting the 2-methoxyestradiol off of the medium with a solvent system comprising a polar solvent and a nonpolar solvent.

15. The method of claim 14, wherein the medium is silica and wherein the 2-methoxyestradiol is eluted using a step gradient of 99:1 CHCl$_3$:MeOH to 98:2 CHCl$_3$:MeOH.

16. A method for producing 2-methoxyestradiol substantially free of steroid contaminants having estrogenic or carcinogenic effects and having a purity greater than 98% and containing less than 0.03% estradiol and less than 0.02% estrone comprising:
protecting the 3- and 17-hydroxyl groups of estradiol;
reacting the protected estradiol with bromine and acetic acid to produce a 2-brominated derivative of estradiol;
reacting the 2-brominated derivative of estradiol with sodium methoxide in the presence of a copper catalyst;
removing the protecting groups on the 3- and 17-hydroxyl groups to produce 2-methoxyestradiol; and
purifying the 2-methoxyestradiol using liquid chromatography on an adsorption/partition medium with a solvent system comprising a polar and a nonpolar solvent.

17. A method for producing 2-methoxyestradiol substantially free of steroid contaminants having estrogenic or carcinogenic effects and having a purity greater than 98% and containing less than 0.03% estradiol and less than 0.02% estrone comprising:
ring-brominating estradiol by reacting estradiol with bromine in the presence of acetic acid to produce a ring-brominated intermediate;

reacting the ring-brominated intermediate with sodium methoxide in the present of a copper catalyst to produce 2-methoxyestradiol; and purifying the 2-methoxyestradiol using liquid chromatography on an adsorption/partition medium with a solvent system comprising a polar and a nonpolar solvent.

18. A method for producing 2-methoxyestradiol substantially free of steroid contaminants having estrogenic or carcinogenic effects and having a purity greater than 98% and containing less than 0.03% estradiol and less than 0.02% estrone comprising:

protecting the 3- and 17-hydroxyl groups of estradiol;

reacting the protected estradiol with nitric acid and acetic acid to produce a 2-nitro derivative of estradiol;

reducing the 2-nitro derivative of estradiol to produce the corresponding 2-amino derivative of estradiol;

reacting the 2-amino derivative of estradiol under Sandmeyer conditions to produce a 3-,17-hydroxyl protected 2-methoxyestradiol; and removing the protecting groups on the 3- and 17-hydroxyl groups to produce 2-methoxyestradiol.

19. A method for producing 2-methoxyestradiol substantially free of steroid contaminants having estrogenic or carcinogenic effects and having a purity greater than 98% and containing less than 0.03% estradiol and less than 0.02% estrone comprising:

protecting the 3-hydroxyl group of estrone;

reacting the protected estrone with nitric acid and acetic acid to produce a 2-nitro derivative of estrone;

reducing the 2-nitro derivative of estrone to produce the corresponding 2-amino derivative of estrone;

reacting the 2-amino derivative of estrone under Sandmeyer conditions to produce a 3-hydroxyl protected 2-methoxyestrone;

removing the protecting group on the 3-hydroxyl group to produce 2-methoxyestrone; and reducing the 17-keto group of 2-methoxyestrone to produce 2-methoxyestradiol.

20. A method for producing 2-methoxyestradiol substantially free of steroid contaminants having estrogenic or carcinogenic effects and having a purity greater than 98% and containing less than 0.03% estradiol and less than 0.02% estrone comprising:

brominating estradiol in the presence of acetic acid to produce a mixture of ring-brominated estradiols;

isolating 2-bromoestradiol from the mixture of estradiols; and reacting the 2-bromoestradiol with sodium methoxide in the presence of a copper catalyst to produce 2-methoxyestradiol.

21. A pharmaceutical composition being substantially free of steroid contaminants having estrogenic or carcinogenic effects comprising 2-methoxyestradiol having a purity greater than 98% and containing less than 0.03% estradiol and less than 0.02% estrone produced by the process comprising:

protecting the 3- and 17-hydroxyl groups of estradiol;

reacting the protected estradiol with bromine and acetic acid to produce a 2-brominated derivative of estradiol;

reacting the 2-brominated derivative of estradiol with sodium methoxide in the presence of a copper catalyst;

removing the protecting groups on the 3- and 17-hydroxyl groups to produce 2-methoxyestradiol; and purifying the 2-methoxyestradiol using liquid chromatography on an adsorption/partition medium with a solvent system comprising a polar and a nonpolar solvent.

22. A pharmaceutical composition being substantially free of steroid contaminants having estrogenic or carcinogenic effects comprising 2-methoxyestradiol having a purity greater than 98% and containing less than 0.03% estradiol and less than 0.02% estrone produced by the process comprising:

ring-brominating estradiol by reacting estradiol with bromine in the presence of acetic acid to produce a ring-brominated intermediate;

reacting the ring-brominated intermediate with sodium methoxide in the presence of a copper catalyst to produce 2-methoxyestradiol; and purifying the 2-methoxyestradiol using liquid chromatography on an adsorption/partition medium with a solvent system comprising a polar and a nonpolar solvent.

23. A pharmaceutical composition being substantially free of steroid contaminants having estrogenic or carcinogenic effects comprising 2-methoxyestradiol having a purity greater than 98% and containing less than 0.03% estradiol and less than 0.02% estrone produced by the process comprising:

protecting the 3- and 17-hydroxyl groups of estradiol;

reacting the protected estradiol with nitric acid and acetic acid to produce a 2-nitro derivative of estradiol;

reducing the 2-nitro derivative of estradiol to produce the corresponding 2-amino derivative of estradiol;

reacting the 2-amino derivative of estradiol under Sandmeyer conditions to produce a 3-,17-hydroxyl protected 2-methoxyestradiol; and removing the protecting groups on the 3- and 17-hydroxyl groups to produce 2-methoxyestradiol.

24. A pharmaceutical composition being substantially free of steroid contaminants having estrogenic or carcinogenic effects comprising 2-methoxyestradiol having a purity greater than 98% and containing less than 0.03% estradiol and less than 0.02% estrone produced by the process comprising:

protecting the 3-hydroxyl group of estrone;

reacting the protected estrone with nitric acid and acetic acid to produce a 2-nitro derivative of estrone;

reducing the 2-nitro derivative of estrone to produce the corresponding 2-amino derivative of estrone;

reacting the 2-amino derivative of estrone under Sandmeyer conditions to produce a 3-hydroxyl protected 2-methoxyestrone;

removing the protecting group on the 3-hydroxyl group to produce 2-methoxyestrone; and reducing the 17-keto group of 2-methoxyestrone to produce 2-methoxyestradiol.

25. A pharmaceutical composition being substantially free of steroid contaminants having estrogenic or carcinogenic effects comprising 2-methoxyestradiol having a purity greater than 98% and containing less than 0.03% estradiol and less than 0.02% estrone produced by the process comprising:

brominating estradiol in the presence of acetic acid to produce a mixture of ring-brominated estradiols;

isolating 2-bromoestradiol from the mixture of estradiols; and reacting the 2-bromoestradiol with sodium methoxide in the presence of a copper catalyst to produce 2-methoxyestradiol.

* * * * *